United States Patent
Dudley, Jr.

(10) Patent No.: US 9,211,301 B2
(45) Date of Patent: *Dec. 15, 2015

(54) METHOD FOR AMELIORATING OR PREVENTING ARRHYTHMIC RISK ASSOCIATED WITH CARDIOMYOPATHY BY IMPROVING CONDUCTION VELOCITY

(75) Inventor: Samuel C. Dudley, Jr., Chicago, IL (US)

(73) Assignees: U.S. DEPARTMENT OF VETERANS AFFAIRS, Washington, DC (US); THE BOARD OF TRUSTEES OF THE UNIV. OF ILLINOIS, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/585,396

(22) Filed: Aug. 14, 2012

(65) Prior Publication Data

US 2012/0308542 A1 Dec. 6, 2012

Related U.S. Application Data

(63) Continuation-in-part of application No. 12/929,786, filed on Feb. 16, 2011, now Pat. No. 9,114,151, and a continuation-in-part of application No. 12/289,005, filed on Oct. 17, 2008, now Pat. No. 8,003,324.

(60) Provisional application No. 61/305,668, filed on Feb. 18, 2010, provisional application No. 60/960,883, filed on Oct. 18, 2007.

(51) Int. Cl.
  *A61K 31/675* (2006.01)
  *A61K 31/7084* (2006.01)

(52) U.S. Cl.
  CPC .................................. *A61K 31/7084* (2013.01)

(58) Field of Classification Search
  CPC .. A61K 31/7084; A61K 31/675; A61P 39/06; A61P 9/00; A61P 9/06
  See application file for complete search history.

(56) References Cited

U.S. PATENT DOCUMENTS

| | | | |
|---|---|---|---|
| 5,668,114 | A | 9/1997 | Birkmayer |
| 5,849,732 | A | 12/1998 | Suzuki et al. |
| 6,339,073 | B1 | 1/2002 | Pero |
| 6,833,371 | B2 | 12/2004 | Atkinson et al. |
| 7,094,600 | B2 | 8/2006 | Wang |
| 7,226,950 | B2 | 6/2007 | Choi et al. |
| 8,003,324 | B2 | 8/2011 | Dudley, Jr. |
| 2004/0091477 | A1 | 5/2004 | Haines et al. |
| 2005/0202093 | A1 | 9/2005 | Kohane et al. |
| 2006/0281668 | A1 | 12/2006 | Parobok et al. |
| 2007/0212723 | A1 | 9/2007 | Dudley et al. |
| 2008/0032940 | A1* | 2/2008 | Kalyanaraman et al. ....... 514/34 |
| 2008/0075666 | A1 | 3/2008 | Dudley et al. |
| 2011/0144192 | A1 | 6/2011 | Dudley, Jr. |
| 2011/0288044 | A1 | 11/2011 | Dudley, Jr. |
| 2012/0288486 | A1 | 11/2012 | Dudley, Jr. |
| 2012/0289482 | A1 | 11/2012 | Dudley, Jr. |

FOREIGN PATENT DOCUMENTS

| | | |
|---|---|---|
| WO | WO 96/19225 A1 | 6/1996 |
| WO | WO 2007/098065 A1 | 7/2009 |
| WO | WO 2010/129964 A1 | 11/2010 |

OTHER PUBLICATIONS

Sovari et al., Journal of Investigative Medicine, (Apr. 2011) vol. 59, No. 4, pp. 693-694. Abstract No. 6. Meeting Info: 2011 Combined Annual Meeting of the American Federation for Medical Research. Chicago, IL, United States. Apr. 14, 2011-Apr. 15, 2011.*
Liu et al., Biophysical Society Meeting Abstracts 2010, Biophysical Journal, Supplement p. 7a.*
Murphy et al., Annu. Rev. Pharmacol. Toxicol. 2007, 47:629-56.*
Alexis Biochemicals Catalog, pp. 1-48, published Apr. 2007.*
Bardy GH, Lee KL, Mark DB, Poole JE, Packer DL, Boineau R et al. Amiodarone or an implantable cardioverter-defibrillator for congestive heart failure. N Engl J Med 2005;352:225-37.
Kamphuis HCM, de Leeuw JRJ, Derksen R, Hauer RNW, Winnubst JAM. Implantable cardioverter defibrillator recipients: quality of life in recipients with and without ICD shock delivery. Europace 2003;5:381-9.
Thomas SA, Friedmann E, Kao CW, Inguito P, Metcalf M, Kelley FJ et al. Quality of life and psychological status of patients withIlmplantable cardioverter defibrillators. Am J Crit Care 2006;15:389-98.
Valdivia CR, Chu WW, Pu J, Foell JD, Haworth RA, Wolff MR et al. Increased late sodium current in myocytes from a canine heart failure model and from failing human heart. J Mol Cell Cardiol 2005;38:475-83.
Ufret-Vincenty CA, Baro DJ, Lederer WJ, Rockman HA, Quinones LE, Santana LF. Role of sodium channel deglycosylation in the genesis of cardiac arrhythmias in heart failure. J Biol Chem 2001;276:28197-203.
Pu J, Boyden PA. Alterations of Na+ currents in myocytes from epicardial border zone of the infarcted heart. A possible ionic mechanism for reduced excitability and postrepolarization refractoriness. Circ Res 1997;81:110-9 (18 pgs), with supplement (15 pgs).
Baba S, Dun W, Boyden PA. Can PKA activators rescue Na+ channel function in epicardial border zone cells that survive in the infarcted canine heart? Cardiovasc Res 2004;64:260-7 (21 pgs), with supplement (17 pgs).
Shaw RM, Rudy Y. Ionic mechanisms of propagation in cardiac tissue: roles of the sodium and L-type calcium currents during reduced excitability and decreased gap junction coupling. Circ Res 1997;81:727-41.
Liu M, Sanyal S, Gao G, Gurung IS, Zhu X, Gaconnet G et al. Cardiac Na+ current regulation by pyridine nucleotides. Circ Res 2009;105:737-45, with supplement (16 pgs).

(Continued)

*Primary Examiner* — Doug Schultz
(74) *Attorney, Agent, or Firm* — Dinesh Agarwal, P.C.

(57) ABSTRACT

A method for reducing arrhythmic risk associated with cardiomyopathy by improving conduction velocity, includes administering a composition containing $NAD^+$ or a mitochondrial targeted antioxidant to an individual or person in need thereof.

24 Claims, 8 Drawing Sheets
(2 of 8 Drawing Sheet(s) Filed in Color)

(56) References Cited

OTHER PUBLICATIONS

Liu M, Liu H, Dudley SC, Jr. Reactive oxygen species originating from mitochondria regulate the cardiac sodium channel. Circ Res 2010;107:967-74, with supplement (10 pgs).
Aon MA, Cortassa S, Marban E, O'Rourke B. Synchronized whole cell oscillations in mitochondrial metabolism triggered by a local release of reactive oxygen species in cardiac myocytes. J Biol Chem 2003;278:44735-44, with supplement (9 pgs).
Di LF, Menabo R, Canton M, Barile M, Bernardi P. Opening of the mitochondrial permeability transition pore causes depletion of mitochondrial and cytosolic NAD+ and is a causative event in the death of myocytes in postischemic reperfusion of the heart. J Biol Chem 2001;276:2571-5.
Silberman GA, Fan T-H, Liu H, Jiao Z, Xiao HD, Lovelock JD et al. Uncoupled cardiac nitric oxide synthase mediates diastolic dysfunction. Circulation 2010;121:519-28, with supplement (21 pgs).
O'Connor DT, Rodrigo M, Simpson P. Isolation and culture of adult mouse cardiac myocytes. Methods Mol Biol 2007;357:271-96.
Bogdanov KY, Vinogradova TM, Lakatta EG. Sinoatrial nodal cell ryanodine ceceptor and Na+-Ca2+ exchanger : molecular partners in pacemaker regulation. Circ Res 2001;88:1254-8.
London B, Michalec M, Mehdi H, Zhu X, Kerchner L, Sanyal S et al. Mutation in Glycerol-3-Phosphate Dehydrogenase 1-Like Gene (GPD1-L) Decreases Cardiac Na+ Current and Causes Inherited Arrhythmias. Circulation 2007;116:2260-8.
Lou Q, Fedorov VV, Glukhov AV, Moazami N, Fast VG, Efimov IR. Transmural heterogeneity and remodeling of ventricular excitation-contraction coupling in human heart failure / clinical perspective. Circulation 2011;123:1881-90, with supplement (12 pgs).
Fedorov VV, Glukhov AV, Ambrosi CM, Kostecki G, Chang R, Janks D et al. Effects of KATP channel openers diazoxide and pinacidil in coronary-perfused atria and ventricles from failing and non-failing human hearts. J Mol Cell Cardiol 2011;51:215-25.
Laughner JI, Sulkin MS, Wu Z, Deng CX, Efimov IR. Three potential mechanisms for failure of high intensity focused ultrasound ablation in cardiac tissue/clinical perspective. Circ: Arrhythm Electrophysiol 2012;5:409-16.
Bayly P, KenKnight B, Rogers J, Hillsley R, Ideker R, Smith W. Estimation of conduction velocity vector fields from epicardial mapping data. IEEE Trans Biomed Eng 1998;45:563-71.
Landmesser U, Dikalov S, Price SR, McCann L, Fukai T, Holland S et al. Oxidation of tetrahydrobiopterin leads to uncoupling of endothelial cell nitric oxide synthase in hypertension. J Clin Invest 2003;111:1201-9.
Glukhov AV, Fedorov VV, Kalish PW, Ravikumar VK, Lou Q, Janks D et al. Conduction remodeling in human end-stage nonischemic left ventricular cardiomyopathy/clinical perspective. Circulation 2012;125:1835-47, with supplement (27 pgs).
Abriel H. Cardiac sodium channel Nav1.5 and its associated proteins. Arch Mal Coeur Vaiss 2007;100:787-93.
Shibata EF, Brown TL, Washburn ZW, Bai J, Revak TJ, Butters CA. Autonomic regulation of voltage-gated cardiac ion channels. J Cardiovasc Electrophysiol 2006;17 Suppl 1:S34-S42.
Akai J, Makita N, Sakurada H, Shirai N, Ueda K, Kitabatake A et al. A novel SCN5A mutation associated with idiopathic ventricular fibrillation without typical ECG findings of Brugada syndrome. FEBS Lett 2000;479:29-34.
Brugada P, Brugada R, Brugada J. The Brugada syndrome. Curr Cardiol Rep 2000;2:507-14.
Makiyama T, Akao M, Tsuji K, Doi T, Ohno S, Takenaka K et al. High risk for bradyarrhythmic complications in patients with Brugada syndrome caused by SCN5A gene mutations. J Am Coll Cardiol 2005;46:2100-6.
Beswick RA, Zhang H, Marable D, Catravas JD, Hill WD, Webb RC. Long-term antioxidant administration attenuates mineralocorticoid hypertension and renal inflammatory response. Hypertension 2001;37:781-6.
Beswick RA, Dorrance AM, Leite R, Webb RC. NADH/NADPH oxidase and.superoxide production in the mineralocorticoid hypertensive rat. Hypertension 2001;38:1107-11, with supplement (3 pgs).
Dikalova AE, Bikineyeva AT, Budzyn K, Nazarewicz RR, McCann L, Lewis W et al. Therapeutic targeting of mitochondrial superoxide in hypertension. Circ Res 2010;107:106-16, with supplement (24 pgs).
Schreibmayer W, Dascal N, Lotan I, Wallner M, Weigl L. Molecular mechanism of protein kinase C modulation of sodium channel α-subunits expressed in Xenopus oocytes. FEBS Lett 1991;291:341-4.
Murphy E, Steenbergen C. Preconditioning: the mitochondrial connection. Annu Rev Physiol 2007;69:51-67, with contents (3 pgs).
Barth E, Stämmler G, Speiser B, Schaper J. Ultrastructural quantitation of mitochondria and myofilaments in cardiac muscle from 10 different animal species including man. J Mol Cell Cardiol 1992;24:669-81.
Das DK, Maulik N. Mitochondrial function in cardiomyocytes: target for cardioprotection. Curr Opin Anaesthesiol 2005;18:77-82.
Duchen MR. Contributions of mitochondria to animal physiology: from homeostatic sensor to calcium signalling and cell death. J Physiol 1999;516:1-17.
Ide T, Tsutsui H, Kinugawa S, Utsumi H, Kang D, Hattori N et al. Mitochondrial electron transport complex I is a potential source of oxygen free radicals in the failing myocardium. Circ Res 1999;85:357-63.
Andrukhiv A, Costa ADT, West I, Garlid KD. Opening mitoKATP increases superoxide generation from complex I of the electron transport chain. Am J Physiol Heart Circ Physiol 2006;291:H2067-H2074.
Eaton P. Protein thiol oxidation in health and disease: techniques for measuring disulfides and related modifications in complex protein mixtures. Free Radic Biol Med 2006:40:1889-99.
Winterbourn CC. Reconciling the chemistry and biology of reactive oxygen species. Nat Chem Biol 2008;4:278-86.
Santos CXC, Anilkumar N, Zhang M, Brewer AC, Shah AM. Redox signaling in cardiac myocytes. Free Radic Biol Med 2011;50:777-93.
Lovelock JD, Monasky MM, Jeong EM, Lardin HA, Liu H, Patel BG et al. Ranolazine improves cardiac diastolic dysfunction through modulation of myofilament calcium sensitivity. Circ Res 2012;1. 10:841-50, with supp. (16 pgs).
Zhou J, Shin HG, Yi J, Shen W, Williams CP, Murray KT. Phosphorylation and putative ER retention signals are required for protein kinase A-mediated potentiation of cardiac sodium current. Circ Res 2002;91:540-6, with supplement (1 pg).
Tateyama M, Kurokawa J, Terrenoire C, Rivolta I, Kass RS. Stimulation of protein kinase C inhibits bursting in disease-linked mutant human cardiac sodium channels. Circulation 2003;107:3216-22.
Epstein AE, DiMarco JP, Ellenbogen KA, Estes III Nam, Freedman RA, Gettes LS et al. ACC/AHA/HRS 2008 guidelines for device-based therapy of cardiac rhythm abnormalities: a report of the American College of Cardiology/American Heart Association Task Force on practice guidelines (writing committee to revise the ACC/AHA/NASPE 2002 guideline update for implantation of cardiac pacemakers and antiarrhythmia devices) developed in collaboration with the American Association for Thoracic Surgery and Society of Thoracic Surgeons. J Am Coll Cardiol 2008;117:e350-e408,with correction (2 pgs).
Ruan Y, Liu N, Priori SG. Sodium channel mutations and arrhythmias. Nat Rev Cardiol 2009;6:337-48.
Abriel H, Kass RS. Regulation of the voltage-gated cardiac sodium channel Na$_v$1.5 by interacting proteins. *Trends Cardiovasc Med* 2005;15(1):35-40.
Zicha S, Maltsev VA, Nattel S, Sabbah HN, Undrovinas AI. Post-transcriptional alterations in the expression of cardiac Na$^+$ channel subunits in chronic heart failure. *J Mol Cell Cardiol* 2004;37(1):91-100.
Bruzzone S, Moreschi I, Guida L, Usai C, Zocchi E, De-áflora A. Extracellular NAD$^+$ regulates intracellular calcium levels and induces activation of human granulocytes. *Biochem J* 2006;393(3):697-704.

(56) References Cited

OTHER PUBLICATIONS

Romanello M, Padoan M, Franco L, Veronesi V, Moro L, D'Andrea P. Extracellular $NAD^+$ induces calcium signaling and apoptosis in human osteoblastic cells. *Biochem Biophys Res Commun* 2001;285(5):1226-31.

Bobalova J, Mutafova-Yambolieva VN. Activation of the adenylyl cyclase/protein kinase A pathway facilitates neural release of β-nicotinamide adenine dinucleotide in canine mesenteric artery. *Eur J Pharmacol* 2006;536(1-2):128-32.

Technikova-Dobrova Z, Sardanelli A, Speranza F, Scacco S, Signorile A, Lorusso V, Papa S. Cyclic adenosine monophosphate-dependent phosphorylation of mammalian mitochondrial proteins: enzyme and substrate characterization and functional role. *Biochemistry* 2001;40:13941-7.

Xie GH, Rah SY, Kim SJ, Nam TS, Ha KC, Chae SW, Im MJ, Kim UH. ADP-ribosyl cyclase couples to cyclic AMP signaling in the cardiomyocytes. *Biochem Biophys Res Commun* 2005;330(4):1290-8.

Zhang F, Jin S, Yi F, Xia M, Dewey WL, Li PL. Local production of $O_2^-$ by NAD(P)H oxidase in the sarcoplasmic reticulum of coronary arterial myocytes: cADPR-mediated $Ca^{2+}$ regulation. *Cell Signal* 2008;20(4):637-44.

Deng N, Zhang J, Zong C, Wang Y, Lu H, Yang P, Wang W, Young GW, Wang Y, Korge P, Lotz C, Doran P, Liem DA, Apweiler R, Weiss JN, Duan H, Ping P. Phosphoproteome analysis reveals regulatory sites in major pathways of cardiac mitochondria. *Mol Cell Proteomics* 2011;10(2):M110.000117 (14 pgs).

Kohlhaas M, Liu T, Knopp A, Zeller T, Ong MF, Böhm M, O'Rourke B, Maack C. Elevated cytosolic $Na^+$ increases mitochondrial formation of reactive oxygen species in failing cardiac myocytes. *Circulation* 2010;121(14):1606-13, with supplement (10 pgs).

Sovari AA, Rutledge CA, Jeong E-M, Dolmatova E, Arasu D, Liu H, Vandani N, Gu L, Zandieh S, Xiao L, Bonini MG, Duffy HS, Dudley SC. Mitochondria-Targeted Antioxidant Therapy Prevents Connexin 43 Remodeling and Sudden Death Caused by Renin-Angiotensin System Activation. *Circulation*. 2012; 126: A19711 (3 pages).

Sovari AA, Jeong EM, Zandieh S, Gu L, Iravanian S, Bonini M, Dudley SC. Mitochondria-Targeted Antioxidant Therapy Prevents Angiotensin II Medicated Connexin 43 Remodeling and Sudden Arrhythmic Death. *Circulation*, vol. 124 (21 Meeting Abs.) Supp. 1, Nov. 22, 2011. Abstract 15801 (1 pg).

Brugada P, Brugada J. Right bundle branch block, persistent ST segment elevation and sudden cardiac death: a distinct clinical and electrocardiographicsyndrome. A multicenter report. *J Am Coll Cardiol*. 1992;20:1391-1396.

Kadish, A. et al. 2006. Patients with recently diagnosed nonischemic cardiomyopathy benefit from implantable cardioverter-defbrillators. *J. Am Coll. Cardiol.* 47:2477-2482.

Amin AS, Verkerk AO, Bhuiyan ZA, Wilde AAM, Tan HL. Novel Brugada syndrom-causing mutation in ion-conducting pore of cardiac Na_ channel does not affect ion selectivity properties. *Acta Physiol Scand*. 2005;185:291-301.

Baroudi G, Napolitano C, Priori SG, Del Bufalo A, Chahine M. Loss of function associated with novel mutations of the SCN5A gene in patients with Brugada syndrome. *Can J Cardiol*. 2004;20:425-430.

Baroudi G, Acharfi S, Larouche C, Chahine M. Expression and Intracellular localization of an SCN5A double mutant R1232W/T1620M implicated in Brugada syndrome. *Circ Res*. 2002;90:e11-e16.

Baroudi G, Pouliot V, Denjoy I, Guicheney P, Shrier A, Chahine M. Novel mechanism for Brugada syndrome: Defective surface localization of an SCN5A mutant (R1432G). *Circ Res*. 2001;88:e78-e83.

Vatta M, Dumaine R, Antzelevitch C, Brugada R, Li H, Bowles NE, Nademanee K, Brugada J, Brugada P, Towbin JA. Novel mutations in domain I of SCN5A cause Brugada syndrome. *Mol Genet Metab*. 2002;75:317-324.

London B, Michalec M, Mehdi H, Zhu X, Kerchner L, Sanyal S, Viswanathan PC, Pfahnl AE, Shang LL, Madhusudanan M, Baty CJ, Lagana S, Aleong R, Gutmann R, Ackerman MJ, McNamara DM, Weiss R, Dudley SC Jr. Mutation in glycerol-3-phosphate dehydrogenase 1-like gene (GPD1-L) decreases cardiac Na_ current and causes inherited arrhythmias. *Circulation*. 2007;116:2260-2268.

Van Norstrand DW, Valdivia CR, Tester DJ, Ueda K, London B, Makielski JC, Ackerman MJ. Molecular and functional characterization of novel glycerol-3-phosphate dehydrogenase 1 like gene (GPD1-L) mutations in sudden infant death syndrome. *Circulation*. 2007;116:2253-2259.

Shen, W. et al. 2006. Involvement of glycerol-3-phosphate dehydrogenase in modulating the NADH/NAD+ ratio provides evidence of a mitochondrial glycerol-3-phosphate shuttle in Arabidopis. *Plant Cell*. 18:422-441.

Papadatos GA, Wallerstein PMR, Head CEG, Ratcliff R, Brady PA, Benndorf K, Saumarez RC, Trezise AEO, Huang CLH, Vandenberg JI, Colledge WH, Grace AA. Slowed conduction and ventricular tachycardia after targeted disruption of the cardiac sodium channel gene SCN5a. *Proc Natl Acad Sci U S A*. 2002;99:6210-6215.

Knollmann BC, Schober T, Petersen AO, Sirenko SG, Franz MR. Action potential characterization in intact mouse heart: steady-state cycle length dependence and electrical restitution. *Am J Physiol Heart Circ Physiol*. 2007;292:H614-H621.

Killeen MJ, Thomas G, Gurugn IS, Goddard CA, Fraser JA, Mahaut-Smith MP, Colledge WH, Grace AA, Huang CLH. Arrhythmogenic mechanisms in the isolated perfused hypokalaemic murine heart. *Acta Physiol*. 2007;189:33-46.

Zalba, G. et al. 2000. Vascular NADH/NADPH oxidase is involved in enhanced superoxide production in spontaneously hypertensive rats. *Hypertension*. 35:1055-1061.

Javesghani, D. et al. 2002. Molecular characterization of a superoxide-generating NAD(P)H oxidase in the ventilator muscles. *Am. J. Respir. Crit. Care Med.* 165: 412-418.

Zicha, S. Maltsev, V.A., Nattel, S., Sabbah, H.N. and Undrovinas, A.L. 2004. Posttranscriptional alterations in the expression of cardiac Na+ channel subunits in chronic heart failure. *J. Mol. Cell. Cardiol.* 37: 91-100.

Schreibmayer W, Dascal N, Lotan I, Wallner M, Weigl L. Molecular mechanism of protein kinase C modulation of sodium channel_-subunits expressed in Xenopus oocytes. *FEBS Lett*. 1991;291:341-344.

Ward, C.A., and Giles, W.R. 1997. Ionic mechanism of the effects of hydrogen peroxide in rat ventricular myocytes. *J. Physiol*. 500: 631-642.

Takeishi, Y., Jalili, T., Ball, N.A. and Walsh, R.A. 1999. Responses of cardiac protein kinase C isoforms to distinct pathological stimuli are differently regulated. *Circ. Res.* 85: 264-271.

Sharma, A. and Singh, M. 2001. Protein kinase C activation and cardioprotective effect of preconditioning with oxidative stress in isolated rat heart. *Mol. Cell. Biochem.* 219: 1-6.

Brawn, M.K., Chiou, W.J. and Leach, K.L. 1995. Oxidant-induced activation of protein kinase C in UC11Mg cells. *Free Radic. Res.* 22: 23-37.

Pfahnl AE, Viswanathan PC, Weiss R, Shang LL, Sanyal S, Shusterman V, Kornblit C, London B, Dudley SC Jr. A sodium channel pore mutation causing Brugada syndrome. *Heart Rhythm*. 2007;4:46-53.

Kyndt, F. et al. 2001. Novel SCN5A mutation leading either to isolated cardiac conduction defect or Brugada syndrome in a large French family. *Circulation*. 104:3081-3086.

Tipparaju SM, Saxena N, Liu SQ, Kumar R, Bhatnagar A. Differential regulation of voltage-gated K_ channels by oxidized and reduced pyridine nucleotide coenzymes. *Am J Physiol Cell Physiol*. 2005;288: C366-C376.

Tipparaju SM, Liu SQ, Barski OA, Bhatnagar A. NADPH binding to _-subunit regulates inactivation of voltage-gated K_ channels. *Biochem Biophys Res Commun*. 2007;359:269-276.

Heiner I, Eisfeld J, Halaszovich CR, Wehage E, Jüngling E, Zitt C Lückhoff A. Expression profile of the transient receptor potential (TRP) family in neutrophil granulocytes: evidence for currents through long TRP channel 2 induced by ADP-ribose and NAD. *Biochem J*. 2003;371: 1045-1053.

(56) References Cited

OTHER PUBLICATIONS

Herson PS, Dulock KA, Ashford ML. Characterization of a nicotinamideadenine dinucleotide-dependent cation channel in the CRI-G1 rat insulinoma cell line. *J Physiol.* 1997;505:65-76.

Alvarez J, Camaleno J, Garcia-Sancho J, Herreros B. Modulation of Ca2_-dependent K_ transport by modifications of the NAD_/ NADH ratio in intact human red cells. *Biochim Biophys Acta.* 1986;856: 408-411.

Zima AV, Copello JA, Blatter LA. Effects of cytosolic NADH/NAD_ levels on sarcoplasmic reticulum Ca2_release in permeabilized rat ventricular myocytes. *J Physiol.* 2004;555:727-741.

Park MK, Lee SH, Ho WK, Earm YE. Redox agents as a link between hypoxia and the responses of ionic channels in rabbit pulmonary vascular smooth muscle. *Exp Physiol.* 1995;80:835-842.

Aon MA, Cortassa S, Marban E, O'Rourke B. Synchronized whole cell oscillations in mitochondrial metabolism triggered by a local release of reactive oxygen species in cardiac myocytes. *J Biol Chem.* 2003;278: 44735-44744.

Di LF, Menabo R, Canton M, Barile M, Bernardi P. Opening of the mitochondrial permeability transition pore causes depletion of mitochondrial and cytosolic NAD_ and is a causative event in the death of myocytes in postischemic reperfusion of the heart. *J Biol Chem.* 2001; 276:2571-2575.

Choudhary G, Dudley SC Jr. Heart failure, oxidative stress, and ion channel modulation. *Congest Heart Fail.* 2002;8:148-155.

Pillai JB, Isbatan A, Imai SI, Gupta MP. Poly(ADP-ribose) polymerase-1-dependent cardiac myocyte cell death during heart failure is mediated by NAD_ depletion and reduced Sir2_ deacetylase activity. *J Biol Chem.* 2005;280:43121-43130.

Dzhanashiya PK, Vladytskaya OV, Salibegashvili NV. Efficiency and mechanisms of the antioxidant effect of standard therapy and refracterin in the treatment of chronic heart failure in elderly patients with postinfarction cardiosclerosis. *Bull Exp Biol Med.* 2004;138:412-414.

Shang LL, Pfahnl AE, Sanyal S, Jiao Z, Allen J, Banach K, Fahrenbach J, Weiss D, Taylor WR, Zafari AM, Dudley SC Jr. Human heart failure is associated with abnormal C-terminal splicing variants in the cardiac sodium channel. *Circ Res.* 2007;101:1146-1154, and Online Supplement (pp. 1-10).

Makielski JC, Farley A. Na_ current in human ventricle: implications for sodium loading and homeostasis. *J Cardiovasc Electrophysiol.* 2006;17: S15-S20.

Valdivia CR, Chu WW, Pu J, Foell JD, Haworth RA, Wolff MR, Kamp TJ, Makielski JC. Increased late sodium current in myocytes from a canine heart failure model and from failing human heart. *J Mol Cell Cardiol.* 2005;38:475-483.

Ajiro Y, Hagiwara N, Kasanuki H. Assessment of markers for idendifying patients at risk for life-threatening arrhythmic events in Brugada syndrome. *J Cardiovasc Electrophysiol.* 2005;16:45-51.

Gellens et al. Primary Structure and Functional Expression of the Human Cardiac Tetrodotoxin-Insensitive Voltage-Dependent Sodium-Channel. *Proceedings of the National Academy of Sciences of the United States of America* 89, 554-558 (1992).

Wang et al. Genomic organization of the human SCN5A gene encoding the cardiac sodium channel. *Genomics* 34, 9-16 (1996).

George et al. Assignment of the human heart tetrodotoxin-resistant voltage-gated Sodium channel alpha-subunit gene (SCN5A) to band 3p21. *Cytogenet. Cell Genet.* 68, 67-70 (1995).

Schott et al. Cardiac conduction defects associate with mutations in SCN5A. *Nat. Genet.* 23, 20-21 (1999).

Tan et al. A calcium sensor in the sodium channel modulates cardiac excitability. *Nature* 415, 442-447 (2002).

Zubay, Biochemistry, Chapter 10, part II Carbohydrate metabolism and chemical energy, p. 400-403 (1984).

Remington's Pharmaceutical Sciences, Mace Publishing Company, Philadelphia, PA., 17th ed. (1985).

Alings, M. and Wilde A. "Brugada" Syndrome: Clinical Data and Suggested Pathophysiological Mechanism. *Circulation* 1999; 99:666-673.

Brugada J, Brugada R, Antzelevitch C et al. Long-term follow-up of individuals with the electrocardiographic pattern of right bundle-branch block and ST-segment elevation in precordial leads V1 to V3. *Circulation.* 2002;105:73-78.

Zhou, M. Diwu Z., Panchuk-Voloshina, N. and Haugland. A Stable Nonfluorescent Derivative of Resorufin for the Fluorometric Determination of Trace Hydrogen Peroxide: Applications in Detecting the Activity of Phagocyte NADPH Oxidase and Other Oxidases. *Analytical Biochemistry* 253 (1997) 162-168.

Mohanty, J.G., Jaffe, J.S., Schulman, E.S. and Raible, D.G.. A Highly Sensitive Fluorescent Micro-Assay of H2O Release from Activated Human Leukocytes Using a Dihydroxyphenoxazine Derivative. *Journal of Immunological Methods* 202 (1997) 133-141.

Liu M, Sanyal S, Gao G, Gurung IS, Zhu X, Gaconnet G, Kerchner LJ, Shang LL, Huang CLH, Grace A, London B, Dudley SC, Jr. Cardiac $Na^+$ current regulation by pyridine nucleotides. *Circ Res.* 2009; 105:737-45, Supplemental Material (pp. 1-8), and Author manuscript Cir Res Oct. 2009; 105(8):737-745.

Shaw RM, Rudy Y. Ionic mechanisms of propagation in cardiac tissue: roles of the sodium and L-type calcium currents during reduced excitability and decreased gap junction coupling. *Circ Res.* 1997; 81:727-41.

Shimizu W, Aiba T, Kamakura S. Mechanisms of disease: current understanding and future challenges in Brugada syndrome. *Nat Clin Pract Cardiovasc Med.* 2005; 2:408-14.

Andrukhiv A, Costa ADT, West I, Garlid KD. Opening of $mitoK_{ATP}$ increases superoxide generation from complex I of the electron transport chain. *Am J Physiol Heart Circ Physiol.* 2006; 291:H2067-H2074.

Ide T, Tsutsui H, Kinugawa S, Utsumi H, Kang D, Hattori N, Uchida K, Arimura Ki, Egashira K, Takeshita A. Mitochondrial electron transport complex I is a potential source of oxygen free radicals in the failing myocardium. *Circ Res.* 1999; 85:357-63.

Mallat Z, Philip I, Lebret M, Chatel D, Maclouf J, Tedgui A. Elevated levels of 8-iso-prostaglandin F2a in pericardial fluid of patients with heart failure : a potential role for in vivo oxidant stress in ventricular dilatation and progression to heart failure. *Circulation.* 1998. 97:1536-9.

Hill MF, Singal PK. Right and left myocardial antioxidant responses during heart failure subsequent to myocardial infarction. *Circulation.* 1997; 96:2414-20 (11 pages).

Dhalla AK, Singal PK. Antioxidant changes in hypertrophied and failing guinea pig hearts. *Am J Physiol Heart Circ Physiol.* 1994; 266:H1280-H1285.

Brady N, Hamacher-Brady A, Westerhoff H, Gottlieb R. A wave of reactive oxygen species (ROS)-induced ROS release in a sea of excitable mitochondria. *Antioxid Redox Signal.* 2006; 8:1651-65.

Zorov DB, Filburn CR, Klotz LO, Zweier JL, Sollott SJ. Reactive oxygen species (ROS)-induced ROS release: a new phenomenon accompanying induction of the mitochondrial permeability transition in cardiac myocytes. *J Exp Med.* 2000; 192:1001-14.

Costa ADT, Pierre SV, Cohen MV, Downey JM, Garlid KD. cGMP signalling in pre- and post-conditioning: the role of mitochondria. *Cardiovasc Res.* 2008; 77:344-52.

Ogbi M, Chew CS, Pohl J, Stuchlik O, Ogbi S, Johnson JA. Cytochrome c oxidase subunit IV as a marker of protein kinase Ce function in neonatal cardiac myocytes: implications for cytochrome c oxidase activity. *Biochem J.* 2004; 382:923-32.

Clarke SJ, McStay GP, Halestrap AP. Sanglifehrin A Acts as a Potent Inhibitor of the Mitochondrial Permeability Transition and Reperfusion Injury of the Heart by Binding to Cyclophilin-D at a Different Site from Cyclosporin A. *J Biol Chem* 2002;277:34793-9.

Sato T, O'Rourke B, Marban E. Modulation of mitochondrial ATP-dependent $K^+$ channels by protein kinase C. *Circ Res.* 1998; 83:110-4.

O'Rourke B. Evidence for mitochondrial $K^+$ channels and their role in cardioprotection. *Circ Res.* 2004; 94:420-32, and Supplement (pp. 1-6).

Chen Q, Vazquez E, Moghaddas S, Hoppel C, Lesnefsky E. Production of reactive oxygen species by mitochondria. *J Biol Chem.* 2003; 278:36027-31.

(56) References Cited

OTHER PUBLICATIONS

Akar FG, Aon MA, Tomaselli GF, O'Rourke B. The mitochondrial origin of postischemic arrhythmias. *J Clin Invest.* 2005; 115:3527-35.
Murphy MP. How mitochondria produce reactive oxygen species. *Biochem J.* 2009; 417:1-13.
O'Rourke B, Ramza B, Marban E. Oscillations of membrane current and.excitability driven by metabolic oscillations in heart cells. *Science.* 1994;.265:962-6.
Murray KT, Hu N, Daw JR, Shin HG, Watson MT, Mashburn AB, George AL Jr. Functional effects of protein kinase C activation on the human cardiac Na_ channel. *Circ Res.* 1997;80:370-376.
Zhou J, Yi J, Hu N, George AL Jr, Murray KT. Activation of protein kinase a modulates trafficking of the human cardiac sodium channel in Xenopus oocytes. *Circ Res.* 2000;87:33-38.
Hallaq et al. Quantitation of protein kinase A-mediated trafficking of cardiac sodium channels in living cells. Cardiovascular Research 72 (2006) 250-261.
Zhou J, Shin HG, Yi J, Shen W, Williams CP, Murray KT. Phosphorylation and putative ER retention signals are required for protein kinase A-mediated potentiation of cardiac sodium current. *Circ Res.* 2002;91: 540-546.
Zhang F, Jin S, Yi F, Xia M, Dewey WL, Li PL. Local production of O2 by NAD(P)H oxidase in the sarcoplasmic reticulum of coronary arterial myocytes: cADPR-mediated Ca2_ regulation. *Cell Signal.* 2008;20: 637-644.
Nitti et al. PKC signaling in oxidative hepatic damage. Molecular Aspects of Medicine 29 (2008) 36-42.
Bruzzone et al. Extracellular NAD+ regulates intracellular calcium levels and induces activation of human granulocytes. Biochem. J. (2006) 393, 697-704.
Romanello et al. Extracellular NAD1 Induces Calcium Signaling and Apoptosis in Human Osteoblastic Cells. Biochemical and Biophysical Research Communications 285, 1226-1231 (2001).
Budas & Mochly-Rosen. Mitochondrial protein kinase Cε (PKCε): emerging role in cardiac protection from ischaemic damage. Biochemical Society Transactions (2007) vol. 35, part 5, 1052-1054.
Silberman GA, Fan T-H, Liu H, Jiao Z, Xiao HD, Lovelock JD, Boulden B, Widder J, Fredd S, Bernstein KE, Wolska B, Dikalov S, Harrison DG, Dudley SCJr. Uncoupled cardiac nitric oxide synthase mediates diastolic dysfunction. *Circulation.* 2010; 121:519-28, and Supp. Data (21 pp).
Sorescu D, Weiss D, Lassegue B, Clempus RE, Szocs K, Sorescu GP, Valppu L, Quinn MT, Lambeth JD, Vega JD, Taylor WR; Griendling KK. Superoxide production and expression of Nox family proteins in human atherosclerosis. *Circulation.* 2002; 105:1429-35.
Pacher P, Nivorozhkin A, Szabo C. Therapeutic effects of xanthine oxidase inhibitors: Renaissance half a century after the discovery of allopurinol. *Pharmacol Rev.* 2006. 58:87-114.
Kobayashi K, Neely JR. Control of maximum rates of glycolysis in rat cardiac muscle. *Circ Res.* 1979; 44:166-75.
Li Q, Hwang YC, Ananthakrishnan R, Oates PJ, Guberski D, Ramasamy R. Polyol pathway and modulation of ischemia-reperfusion injury in Type 2 diabetic BBZ rat hearts. *Cardiovasc Diabetol.* 2008; 7:33-44 (11 pages).
Moir AM, Zammit VA. Insulin-independent and extremely rapid switch in the partitioning of hepatic fatty acids from oxidation to esterification in starved-refed diabetic rats. *Biochem J.* 1995; 305:953-8.
van Raam B, Sluiter W, de Wit E, Roos D, Verhoeven A, Kuijpers T. Mitochondrial membrane potential in human neutropils is maintained by complex III activity in the absence of supercomplex organisation. *PLoS ONE.* 2008; 3:e2013 (12 pages).
Liang HL, Arsenault J, Mortensen J, Park F, Johnson CP, Nilakanta V. Partial attenuation of cytotoxicity and apoptosis by SOD1 in ischemic renal epithelial cells. *Apoptosis.* 2009; 14:1176-89.
Dikalova AE, Bikineyeva AT, Budzyn K, Nazarewicz RR, McCann L, Lewis W, Harrison DG, Dikalov SI. Therapeutic targeting of mitochondrial superoxide in hypertension. *Circ Res.* 2010; 107:106-16, and Online Supp. (12 pages).

Murphy E, Steenbergen C. Preconditioning: the mitochondrial connection. *Annu Rev Physiol.* 2007; 69:51-67.
Barth E, Stämmler G, Speiser B, Schaper J. Ultrastructural quantitation of mitochondria and myofilaments in cardiac muscle from 10 different animal species including man. *J Mol Cell Cardiol.* 1992; 24:669-81.
Boveris A, Oshino N, Chance B. The cellular production of hydrogen peroxide. *Biochem J.* 1972; 128:617-630.
Batandier C, Fontaine E, Keriel C, Leverve X. Determination of mitochondrial reactive oxygen species: methodological aspects. *J Cell Mol Med.* 2002; 6:175-87.
Panov A, Schonfeld P, Dikalov S, Hemendinger R, Bonkovsky HL, Brooks BR. The Neuromediator glutamate, through specific substrate interactions, enhances mitochondrial ATP production and reactive oxygen species generation in monsynaptic brain mitochondria. *J Biol Chem.* 2009; 284:14448-56.
Han D, Antunes F, Canali R, Rettori D, Cadenas E. Voltage-dependent anion channels control the release of the superoxide anion from mitochondria to cytosol. *J Biol Chem.* 2003; 278:5557-63.
Brown D, Aon MA, Akar FG, Liu T, Sorarrain N, O'Rourke B. Effects of 4'-chlorodiazepam on cellular excitation-constraction coupling and ischaemia-reperfusion injury in rabbit heart. *Cardiovasc Res.* 2008; 79:141-9.
Valdivia CR, Ueda K, Ackerman MJ, Makielski JC. GPD1L links redox state to cardiac excitability by PKC-dependent phosphorylation of the sodium channel SCN5A. *AJP—Heart and Circulatory Physiology.* 2009; 297:H1446-H1452.
Zelent B, Troxler T, Vanderkooi JM. Temperature dependence for fluorescence of β-NADH in glycerol/water solution and in trehalose/sucrose glass. *Journal of Fluorescence.* 2007; 17:37-42.
Liu M, Gaconnet G, London B, Dudley, Jr. S.C. A Central Role of Mitochondria in the Regulation of Sodium Current. Presentation at the Cardiac Electrophysiology Society, Orlando, Florida (Nov. 14, 2009) (1 page).
Yang H, Yang T, Baur JA, Perez E, Matsui T, Carmona JJ, Lamming D, Souza-Pinto NC, Bohr VA, Rosenzweig A, de Cabo R, Sauve A, Sinclair DA. Nutrient-sensitive mitochondrial NAD_ levels dictate cell survival. *Cell.* 2007;130:1095-1107.
Lin SJ, Guarente L. Nicotinamide adenine dinucleotide, a metabolic regulator of transcription, longevity and disease. *Curr Opin Cell Biol.* 2003;15:241-246.
Herbert JM, Augereau JM, Gleye J, Maffrand JP. Chelerythrine is a potent and specific inhibitor of protein kinase C. *Biochem Biophys ResCommun.* 1990;172:993-999.
Chao MD, Chen IS, Cheng JT. Inhibition of protein kinase C translocation from cytosol to membrane by chelerythrine. *Planta Med.* 1998;64: 662-663.
Frohnwieser B, Chen L, Schreibmayer W, Kallen R. Modulation of the human cardiac sodium channel alpha-subunit by cAMP-dependent protein kinase and the responsible sequence domain. *J Physiol* (London). 1997;498:309-318.
Glass DB, Lundquist LJ, Katz BM, Walsh DA. Protein kinase inhibitor-(6-22)-amide peptide analogs with standard and nonstandard amino acid substitutions for phenylalanine 10. Inhibition of cAMP-dependent protein kinase. *J Biol Chem.* 1989;264:14579-14584.
Shirt HG, Murray KT. Conventional protein kinase C isoforms and cross-activation of protein kinase A regulate cardiac Na_ current. *FEBS Lett.* 2001;495:154-158.
Biswas S, DiSilvestre D, Tian Y, Halperin VL, Tomaselli GF. Calciummediated dual-mode regulation of cardiac sodiym channel gating. *Circ Res.* 2009;104:870-878, and Supp. Material (10 pages).
Casini S, Verkerk AO, van Borren MM, van Ginneken AC, Veldkamp MW, de Bakker JM, Tan HL. Intracellular calcium modulation of voltage-gated sodium channels in ventricular myocytes. *Cardiovasc Res.* 2009;81:72-81.
Brisson D, Vohl M, St Pierre J, Hudson T, Gaudet D. Glycerol: a neglected variable in metabolic process? *Bioessays.* 2001;23.6:534-542.
Antzelevitch C, Brugada P, Borggrefe M, et al. Brugada syndrome: report of the second consensus conference: endorsed by the Heart Rhythm Society and the European Heart Rhythm Association. *Circulation.* 2005; 111 :659-670.

(56) References Cited

OTHER PUBLICATIONS

Brugada J, Brugada P. Further characterization of the syndrome of right bundle branch block, ST segment elevation, and sudden cardiac death. *J Cardiovasc Electrophysiol.* 1997; 8:325-331.
Grant AD. Electrophysiological basis and genetics of Brugada syndrome. *J Cardiovasc Electrophysiol.* 2005; 16:S3-7.
Chen Q, Kirsch GE, Zhang 0, et al. Genetic basis and molecular mechanism for idiopathic ventricular fibrillation. *Nature.* 1998; 392:293-296.
Priori SG, Napolitano C, Gasparini M, et al. Clinical and genetic heterogeneity of right bundle branch block and ST -segment elevation syndrome: A prospective evaluation of 52 families. *Circulation.* 2000; 102:2509-2515.
Valdivia CR, Tester OJ, Rok BA, et al. A trafficking defective, Brugada syndromecausing SCNSA mutation rescued by drugs. *Cardiovasc Res.* 2004; 62:53-62.
Brugada R, Brugada J, Antzeievitch G, et al. Sodium channel blockers identify risk for sudden death in patients with ST-segment elevation and right bundle branch block but structurally normal hearts. *Circulation.* 2000; 101:510-515.
Pollevick GO, Schimpf R, Aizawa Y, et al. Loss of function in calcium channel activity secondary to a mutation in CACNB2b modulates the clinical manifestation of a combined Brugada syndrome-hort aT phenotype. *Circulation.* 2006; 114:11-193 (Abstract—3 pages).
Yan GX, Antzelevitch C. Cellular basis for the Brugada syndrome and other mechanisms of arrhythmogenesis associated with ST-segment elevation. *Circulation.* 1999; 100:1660-1666.
Weiss R, Barmada MM, Nguyen T, et al. Clinical and molecular heterogeneity in the Brugada syndrome: a novel gene locus on chromosome 3. *Circulation.* 2002;105:707-713.
Walz AG, Demel RA, de Kruijff S, et al. Aerobic sn-glycerol-3-phosphate dehydrogenase from *Escherichia coli* binds to the cytoplasmic membrane through an amphipathic alpha-helix. *Biochem J.* 2002; 365:471-479.
Myerburg RJ, Castellanos A. Cardiac arrest and sudden cardiac death. In: P. ZD, Libby P, Bonow RO, et al., eds. *Braumwald's Heart disease: A textbook of cardiovascular medicine.* 7th ed. Phildadelphia: Elsevier Saunders; 2005:865-908 (Chapter 33).
Priori SG, Rivolta I, Napolitano C. Genetics of long QT, Brugada, and other channelopathies. In: P. ZD, Jalife J, eds. *Cardiac Electrophysiology. From Cell to Bedside.* 4th ed. Philadelphia: Saunders; 2004:462-470 (Chapter 50).
Sarkozy A, Brugada P. Sudden Cardiac Death and Inherited Arrhythmia Syndromes. J *Cardiovasc Electrophysiol.* 2005; 16:S8-20.
Mohler PJ, Schott JJ, Gramolini AO, et al. Ankyrin-B mutation causes type 4 long-QT cardiac arrhythmia and sudden cardiac death. *Nature.* 2003; 21:634-639.
Corrado 0, Thiene G. Arrhythmogenic right ventricular cardiomyopathy/dysplasia: clinical impact of molecular genetic studies. *Circulation.* 2006; 113:1634-1637.
Schwartz PJ, Priori SG, Dumaine R, et al. A molecular link between the sudden infant death syndrome and the long-QT syndrome. *N. Engl J Med.* 2000;343:262-267.
Van Norstrand OW, Valdivia CR, Tester OJ, et al. Molecular and functional characterization of a novel GPD1-L mutations in sudden Infant Death Syndrome. Circulation 2007; 116-2253-2259.
Royer A, van Veen TA, Le Bouter S, et al. Mouse model of SCNSA-linked hereditary Lenegre's disease: age-related conduction slowing and myocardial fibrosis. *Circulation.* 2005; 111: 1738-1746.
Tan HL, Bink-Boelkens MT, Bezzina CR, et al. A sodium-channel mutation causes isolated cardiac conduction disease. *Nature.* 2001; 409:1043-1047.
Mihm MJ, Yu F, Cames CA, et al. Impaired myofibrillar energetics and oxidative injury during human atrial fibrillation. *Circulation.* 2001; 104:174-180.
Fukuda K, Davies SS, Nakajima T, et al. Oxidative mediated lipid peroxidation recapitulates proarrhythmic effects on cardiac sodium channels. *Circ Res.* 2005; 97:1262-1269.
Rubart M, Zipes DP. Mechanisms of sudden cardiac death. *J Clin Invest.* 200S; 115:2305-2315.
CAST. Preliminary report: effect of encainide and flecainide on mortality in a randomized trial of arrhythmia suppression after myocardial infarction. The Cardiac Arrhythmia Suppression Trial (CAST) Investigators. *N Engl J Med.* 1989; 321 :406-412.
PCT International Search Report and Written Opinion dated Jan. 30, 2009, in International App. No. PCT/US2008/011919 (12 pp.).
Krebs et al. (1999). "Na+ translocation by the NADH:ubiquinone oxidoreductase (complex I) from Klebsiella pneumoniae." Molecular Microbiology 33(2):590-598.
Udagawa et al. (1986). "Generation of Na+ electrochemical potential by the Na+-motive NADH oxidase and Na+/H+ antiport system of a moderately halophilic Vibrio costicola." J. Biol. Chem. 261(6):2616-2622.
Sanyal et al., Circulation. Oct. 16, 2007. 116(16) S185-S186, Abstract 941.
Office Action (Restriction Requirement) dated Jul. 6, 2010, in U.S. Appl. No. 12/289,005, filed Oct. 17, 2008.
Office Action dated Oct. 5, 2010, in U.S. Appl. No. 12/289,005, filed Oct. 17, 2008.
Notice of Allowance dated Jun. 23, 2011, in U.S. Appl. No. 12/289,005, filed Oct. 17, 2008.
Office Action dated Oct. 3, 2011, in co-pending U.S. Appl. No. 13/067,953, filed Jul. 11, 2011.
U.S. Appl. No. 13/067,953, filed Jul. 11, 2011.
U.S. Appl. No. 13/091,972, filed Apr. 21, 2011.
U.S. Appl. No. 11/895,883, filed Aug. 27, 2007.
U.S. Appl. No. 13/507,319, filed Jun. 21, 2012.
U.S. Appl. No. 13/551,790, filed Jul. 18, 2012.
U.S. Appl. No. 11/707,882, filed Feb. 20, 2007.
U.S. Appl. No. 13/658,943, filed Oct. 24, 2012.
Office Action dated Oct. 12, 2012, in U.S. Appl. No. 13/091,972, filed Apr. 21, 2011.
Ouzounian et al. Diastolic heart failure: mechanisms and controversies. Nature Clinical Practice Cardiovascular Medicine. 5(7):375-386, Jul. 2008.
Reed et al. FASEB Journal. The senescence-accelerated mouse: a model for the investigation of age-related oxidative stress and diastolic dysfunction. 22:Meeting Abstract Supplement, Mar. 2008, 970. 39 (2 pages).
Li et al. Aging induces cardiac diastolic dysfunction, oxidative stress, accumulation of advanced glycation endproducts and protein modification. Aging Cell. 4(2):57-64, Apr. 2005.
Westermann et al. Cardiac Inflammation Contributes to Changes in the Extracellular Matrix in Patients with Heart Failure and Normal Ejection Fraction. Circulation Heart Failure. 2011;4:44-52.
Satpathy et al. Diagnosis and management of diastolic dysfunction and heart failure. American Family Physician. 73(5):841-846. Mar. 1, 2006.
Kuwahara et al. Transforming Growth Factor-β Function Blocking Prevents Myocardial Fibrosis and Diastolic Dysfunction in Pressure-Overloaded Rats. Circulation; 106:130-135, 2002.
Leask, Andrew. TGF-β, cardiac fibroblasts, and the fibrotic response. Cardiovascular Research. 74:207-212, Jul. 21, 2006.
Reed et al. Diastolic Dysfuntion is Associated with Cardiac Fibrosis in the Senecence-Accelerated Mouse. Circulation 120(18), Supplement 2, S762-S763, Nov. 3, 2009 (1 page).
Blom et al. Gene regulation of connective tissue growth factor: new targets for antifibrotic therapy? Matrix Biology 21 (2002) 473-482.
Kleber AG. Mechanism of Ventricular Arrhythmias: A Perspective. J. Cardiovascular Pharmacology 17(Suppl. 6):S1-S8, 1991.
Salama G et al. Deciphering Arrhythmia Mechanisms—Tools of the Trade. Card Electrophysiol Clin. Mar. 2011; 3(1):11-21 (15 pages).
Moens AL et al. Myocardial ischemia/reperfuion-injury, a clinical view on a complex pathophysiological process. International Journal of Cardiology 100 (2005) 179-190.
Office Action (Restriction Requirement) dated Jun. 11, 2012, in U.S. Appl. No. 12/929,786, filed Feb. 16, 2011.
Office Action dated Sep. 14, 2012, in U.S. Appl. No. 12/929,786, filed Feb. 16, 2011.
U.S. Appl. No. 12/929,786, filed Feb. 16, 2011.

(56) References Cited

OTHER PUBLICATIONS

Tu YX, Wernsdorfer A, Honda S, Tomita Y. Estimation of Conduction Velocity Distribution by Regularized-Least-Squares Method. IEEE Trans on Biomedical Engineering. vol. 44, No. 11, Nov. 1997: 1102-1106.

Li et al. Targeting mitochondrial reactive oxygen species as novel therapy inflammatory diseases and cancers, Journal of Hematology & Oncology 2013, 6:19 (19 pgs).

Smith et al. Mitochondrial pharmacology, Trends in Pharmacological Sciences, Jun. 2012, vol. 33, No. 6, 341-352.

Sovari et al. Mitochondria Oxidative Stress, Connexin43 Remodeling, and Sudden Arrhythmic Death, *Circ Arrhythm Electrophysiol.* 2013;6:623-631.

Final Rejection dated Mar. 11, 2013, in U.S. Appl. No. 12/929,786, filed Feb. 16, 2011.

Office Action dated Sep. 6, 2013, in U.S. Appl. No. 13/507,319, filed Jun. 21, 2012.

Office Action dated Sep. 6, 2013, in U.S. Appl. No. 13/551,790, filed Jul. 18, 2012.

U.S. Appl. No. 14/083,841, filed Nov. 19, 2013.

Office Action dated Oct. 3, 2013, in U.S. Appl. No. 12/929,786, filed Feb. 16, 2011.

Office Action dated Nov. 5, 2013, in U.S. Appl. No. 13/507,319, filed Jun. 21, 2012.

Office Action dated Nov. 6, 2013, in U.S. Appl. No. 13/551,790, filed Jul. 18, 2012.

Irvanian et al., The Renin-Angiotensin-Aldosterone System (RAAS) and Cardiac Arrhythmias. Heart Rhythm Jun. 2008, 5(6 Supplement 1): s12-s17.

Tomaselli et al., Oxidative stress irritates the heart. Nature Medicine. Jun. 2010, 16:648-649.

http://www.biophysics.org/2010meeting/Registration/RatesDeadlines/tabid/675/Default.aspx.

Liu et al. Mitchondrial dysfunction causing cardiac sodium channel downregulation in cardiomyopathy. *Journal of Molecular and Cellular Cardiology* 54 (2013) 25-34.

Lotrionte et al. Review and Meta-Analysis of Incidence and Clinical Predictors of Anthracycline Cardiotoxicity. *Am J Cardiol* 2013;112:1980-1984.

Mackay et al. Assessment of Anthracycline Cardiomyopathy by Endomycardial Biopsy. Ultrastructural Pathology, 18:203-211, 1994.

Chatterjee et al. Doxorubicin Cardiomyopathy. *Cardiology* 2010; 115:155-162.

De Angelis et al. Anthracycline Cardiomyopathy is Medicated by Depletion of the Cardiac Stem Cell Pool and is Rescued by Restoration of Progenitor Cell Function. *Circulation.* 2010;121:276-292.

Mazevet et al. Complications of chemotherapy, a basic science update. *Presse Med.* 2013; 42; e352-e361.

Octavia et al. Doxorubicin-induced cardiomyopathy: From molecular mechanisms to therapeutic strategies. *Journal of Molecular and Cellular Cardiology* 52 (2012) 1213-1225.

Chanan-Khan et al. Prevention and Management of Cardiotoxicity From Antineoplastic Therapy. *J Support Oncol.* 2004; 2:251-266.

Epstein AE, DiMarco JP, Ellenbogen KA, Estes NA, III, Freedman RA, Gettes LS, Gillinov AM, Gregoratos G, Hammill SC, Hayes DL, Hlatky MA, Newby LK, Page RL, Schoenfeld MH, Silka MJ, Stevenson LW, Sweeney MO, Tracy CM, Epstein AE, Darbar D, DiMarco JP, Dunbar SB, Estes NA, III, Ferguson TB, Jr., Hammill SC, Karasik PE, Link MS, Marine JE, Schoenfeld MH, Shanker AJ, Silka MJ, Stevenson LW, Stevenson WG, Varosy PD. 2012 ACCF/AHA/HRS focused update incorporated into the ACCF/AHA/HRS 2008 guidelines for device-based therapy of cardiac rhythm abnormalities: a report of the American College of Cardiology Foundation/American Heart Association Task Force on Practice Guidelines and the Heart Rhythm Society. *J Am Coll Cardiol* 2013;61:e6-75.

Nakahara S, Tung R, Ramirez RJ, Michowitz Y, Vaseghi M, Buch E, Gima J, Wiener I, Mahajan A, Boyle NG, Shivkumar K. Characterization of the arrhythmogenic substrate in ischemic and nonischemic cardiomyopathy implications for catheter ablation of hemodynamically unstable ventricular tachycardia. *J Am Coll Cardiol* 2010;55:2355-65.

Boriani G, Gasparini M, Lunati M, Santini M, Landolina M, Vincenti A, Curnis A, Bocchiardo M, Padeletti L, Biffi M, Allaria L, Denaro A. Characteristics of ventricular tachyarrhythmias occurring in ischemic versus nonischemic patients implanted with a biventricular cardioverter-defibrillator for primary or secondary prevention of sudden death. *Am Heart J* 2006;152:527-11.

Lindsay BD, Ambos HD, Schechtman KB, Arthur RM, Cain ME. Noninvasive detection of patients with ischemic and nonischemic heart disease prone to ventricular fibrillation. *J Am Coll Cardiol* 1990;16:1656-64.

Rouleau J, Shenasa M, de CJ, Nadeau R. Predictors of survival and sudden death in patients with stable severe congestive heart failure due to ischemic and nonischemic causes: a prospective long term study of 200 patients. *Can J Cardiol* 1990;6:453-60.

Ehlert FA, Cannom DS, Renfroe EG, Greene HL, Ledingham R, Mitchell LB, Anderson JL, Halperin BD, Herre JM, Luceri RM, Marinchak RA, Steinberg JS. Comparison of dilated cardiomyopathy and coronary artery disease in patients with life-threatening ventricular arrhythmias: Differences in presentation and outcome in the AVID registry. *Am Heart J* 2001;142:816-22.

Contractor T, Beri A, Gardiner J, Ardhanari S, Thakur R. Statins reduce appropriate implantable cardioverter-defibrillator shocks in ischemic cardiomyopathy with no benefit in nonischemic cardiomyopathy. *Am J Ther* 2012;19:413-8.

Furushima H, Chinushi M, Okamura K, Komura S, Tanabe Y, Sato A, Izumi D, Aizawa Y. Effect of dl-sotalol on mortality and recurrence of ventricular tachyarrhythmias: ischemic compared to nonischemic cardiomyopathy. *Pacing Clin Electrophysiol* 2007;30:1136-41.

Latif S, Dixit S, Callans DJ. Ventricular arrhythmias in normal hearts. *Cardiol Clin* 2008;26:367-80, vi.

Sadek MM, Marchlinski FE. Ablation of ventricular arrhythmias. *Trends Cardiovasc Med* 2014;24:296-304.

Hoffmayer KS, Gerstenfeld EP. Diagnosis and management of idiopathic ventricular tachycardia. *Curr Probl Cardiol* 2013;38:131-58.

Roberts-Thomson KC, Lau DH, Sanders P. The diagnosis and management of ventricular arrhythmias. *Nat Rev Cardiol* 2011;8:311-21.

Morin DP, Lerman BB. Management of ventricular tachycardia in the absence of structural heart disease. *Curr Treat Options Cardiovasc Med* 2007;9:356-63

Liu M, Liu H, Jeong EM, Gu L, Dudley SC. Mitochondrial reactive oxygen species regulate the cardiac $Na^+$ channel in heart failure. *Basic Cardiovascular Sciences 2011 Scientific Sessions* 2011; Abstract:2011-A-246-AHA-BCVS.

Rutledge CA, Ng FS, Sulkin MS, Greened ID, Sergeyenko AM, Liu H, Gemel J, Beyer EC, Sovari AA, Efimov IR, Dudley SC. c-Src kinase inhibition reduces arrhythmia inducibility and connexin43 dysregulation after myocardial infarction. *J Am Coll Cardiol* 2014;63:928-34.

Davies et al. Redox Cycling of Anthracyclines by Cardiac Mitochondria, 1986, *The Journal of Biological Chemistry*, vol. 261, No. 7, 3068-3074.

World Health Organization (WHO) International Classification of Diseases (ICD) http://www.who.int/classifications/icd/en/ (2 pages) Accessed Jul. 16, 2014.

Cardiomyopathy (I42) and cardiomyopathy due to drug or external agent (I42.7) http://apps.who.int/classifications/icd10/browse/2010/en#/I30-I52 (1 page) Accessed Jul. 16, 2014.

Felker et al., Underlying Cause and Long-Term Survival in Patients with Initially Unexplained Cardiomyopathy. *The New Engalnd Journal of Medicine*, 2000, vol. 342, No. 15, 1077-84.

Octavia Y. et al., Doxorubicin-induced cardiomyopathy: From molecular mechanisms to therapeutic strategies. *Journal of Molecular and Cellular Cardiology*, 52, 2012, 1213-1225.

Guilherme H. et al., Increased Need for Right Ventricular Support in Patients With Chemotherapy-Induced Cardiomyopathy Undergoing Mechanical Circulatory Support. *Journal of the American College of Cardiology,* 2014, vol. 63, No. 3, 240-248.

(56) References Cited

OTHER PUBLICATIONS

Tabane K. et al. Cancer drugs: Highlighting the molecular mechanisms of cardiotoxicity. SA Heart, 2012;9:244-248.
Zhang S. et al., Identification of the molecular basis of doxorubicin-induced cardiotoxicity. *Nature Medicine,* 2012, vol. 18, No. 11, 1639-1642. With Online Methods (3 pgs).
Ichikawa I. et al., Cardiotoxicity of doxorubicin is mediated through mitochondrial iron accumulation. *Journal of Clinical Investigation,* 2014; vol. 124, No. 2:617-630.
Jeyaseelan R. et al., A novel Cardiac-Restricted Target for Doxorubicin. *The Journal of Biological Chemistry,* 1997, vol. 272, No. 36, 22800-22808.
Office Action dated May 14, 2014, in U.S. Appl. No. 12/929,786, filed Feb. 16, 2011.
Office Action dated Jun. 25, 2014, in U.S. Appl. No. 13/551,790, filed Jul. 18, 2012.
Office Action dated Jul. 28, 2014, in U.S. Appl. No. 13/507,319, filed Jun. 21, 2012.

\* cited by examiner

FIG. 6A Preparation

FIG. 6B Optical Action Potentials

FIG. 6C Activation Map

Conduction Velocity

METHOD FOR AMELIORATING OR PREVENTING ARRHYTHMIC RISK ASSOCIATED WITH CARDIOMYOPATHY BY IMPROVING CONDUCTION VELOCITY

CROSS-REFERENCE TO RELATED APPLICATIONS

This is a continuation-in-part (CIP) application of U.S. application Ser. No. 12/929,786, filed Feb. 16, 2011, which claims the priority benefit of U.S. Provisional Patent Application Ser. No. 61/305,668, filed Feb. 18, 2010, and is a continuation-in-part (CIP) application of U.S. application Ser. No. 12/289,005, filed Oct. 17, 2008, now U.S. Pat. No. 8,003,324B2, which claims the priority benefit of U.S. Provisional Patent Application Ser. No. 60/960,883, filed Oct. 18, 2007, all of the foregoing are hereby incorporated herein in their entirety by reference.

STATEMENT REGARDING FEDERALLY SPONSORED RESEARCH OR DEVELOPMENT

The invention was made with government supported under grants R01 HL072742, R01HL106592, R01HL104025, NIH R01HL085369, T32 HL072742, and P01HL058000, and a VA MERIT grant. The government has certain rights in the invention.

FIELD AND BACKGROUND OF THE INVENTION

Despite extensive research and novel treatments, conditions associated with deranged cardiac metabolism, such as heart failure or ischemia, are still accompanied by a substantial risk of arrhythmic sudden death (Reference 1). While implanted cardiac defibrillators have decreased sudden death risk, they can cause physical and psychological complications. They are also expensive, and do not address the underlying pathology that leads to arrhythmic risk (References 2 and 3). A more complete molecular understanding of the basis for the increased arrhythmic risk is likely to lead to new therapies that will be more effective and less invasive.

Cardiac injury from many causes is associated with altered metabolism and downregulation of the cardiac $Na^+$ channel ($Na_v1.5$) (References 4-7). Recently, we reported that an elevation of intracellular reduced nicotinamide adenine dinucleotide (NADH) can downregulate $Na^+$ current ($I_{Na}$) acutely and to a degree that is large enough to be clinically significant (Reference 8). The signaling cascade involves a protein kinase C (PKC)-mediated increase in mitochondrial reactive oxygen species (ROS) production (References 9 and 10). NADH is known to oscillate with myocardial ischemia, and mitochondrial injury is associated with increased NADH and ROS levels (References 11 and 12). These changes could contribute to reduced $I_{Na}$, conduction block, and arrhythmic risk known to exist with reduced cardiac contractility. The NADH effect on ROS production and $I_{Na}$ can be antagonized by PKA activation mediated by $NAD^+$, by superoxide dismutase, or by 2-(2,2,6,6-Tetramethylpiperidin-1-oxyl-4-ylamino)-2-oxoethyl)triphenylphosphonium chloride (Mito-TEMPO), a specific scavenger of mitochondrial ROS (References 9, 10). To evaluate the clinical relevance of this signaling pathway, we tested whether NADH and mitochondrial ROS were elevated in nonischemic cardiomyopathy and whether these changes resulted in a reduction in $I_{Na}$. We also investigated whether $NAD^+$, 2-(2,2,6,6-Tetramethylpiperidin-1-oxyl-4-ylamino)-2-oxoethyl)triphenylphosphonium chloride (MitoTEMPO), PKC inhibitors (a PKC pan inhibitor chelerythrine and δV1-1, a specific inhibitor for PKCδ), or a PKA activator (forskolin) could counteract the effects of NADH on mitochondrial ROS and cardiac $I_{Na}$. To show relevance of the findings, the effect of $NAD^+$ on conduction velocity (CV) in human failing hearts was evaluated.

ASPECTS OF THE INVENTION

The present disclosure is directed to various aspects of the present invention.

One aspect of the present invention includes discovery and/or demonstration that mitochondria are the main source of NADH-dependent ROS downregulating sodium channel current ($I_{Na}$) in cardiomyopathic cells, which adversely affects the conduction velocity.

Another aspect of the present invention includes discovery and/or demonstration that mitochondrial superoxide release is responsible for downregulation of $I_{Na}$ in cardiomyopathic cells, which adversely affects the conduction velocity.

Another aspect of the present invention includes discovery and/or demonstration that elevation in intracellular NADH results in activation of protein kinase C (PKE) and subsequent mitochondrial complex III release of reactive oxygen species (ROS) through the mitochondrial inner member anion channel (IMAC) in cardiomyopathic cells, which adversely affects the conduction velocity.

Another aspect of the present invention includes discovery and/or demonstration that inhibition of mitochondrial ROS overproduction by one or more strategies prevents, suppresses, or reverses $I_{Na}$ downregulation by NADH in cardiomyopathic cells, thereby improving conduction velocity.

Another aspect of the present invention includes suggestions and/or development of possible therapeutic approaches or strategies to reduce or prevent arrhythmic risk associated with cardiomyopathy by improving conduction velocity.

Another aspect of the present invention includes a method for reducing arrhythmic risk associated with cardiomyopathy by improving conduction velocity, including the step of administering a composition containing $NAD^+$ to an individual in need thereof.

Another aspect of the present invention includes a method for improving conduction velocity by restoring the cardiac sodium current to a normal level in an individual with cardiomyopathy, including the step of administering a composition containing $NAD^+$ to an individual in need thereof.

Another aspect of the present invention includes a method for reducing arrhythmic risk in an individual with cardiomyopathy and a cardiac ejection fraction of less than 50% by improving conduction velocity, including the step of administering a composition containing $NAD^+$ to an individual in need thereof.

Another aspect of the present invention includes a method for reducing arrhythmic risk associated with cardiomyopathy by improving conduction velocity, including the step of administering a mitochondrial targeted antioxidant to an individual in need thereof.

Another aspect of the present invention includes a method for improving conduction velocity by restoring the cardiac sodium current to a normal level in an individual with cardiomyopathy, including the step of administering a mitochondrial targeted antioxidant to an individual in need thereof.

Another aspect of the present invention includes a method for reducing arrhythmic risk in an individual with cardiomyopathy and a cardiac ejection fraction of less than 50% by improving conduction velocity, including the step of administering a mitochondrial targeted antioxidant to an individual in need thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

One of the above and other aspects, novel features and advantages of the present invention will become apparent from the following detailed description of the non-limiting preferred embodiment(s) of invention, illustrated in the accompanying drawings, wherein:

FIG. 2A illustrates representative whole cell current traces of $I_{Na}$ from sham and DOCA mouse ventricular cardiomyocytes held at −100 mV and measured from −100 to +60 mV with 10 mV steps;

FIG. 2B illustrates peak $I_{Na}$ from sham and DOCA mice ventricular cardiomyocytes measured at −20 mV. *P<0.01 vs sham;

FIGS. 4A-C illustrate $NAD^+$, 2-(2,2,6,6-Tetramethylpiperidin-1-oxyl-4-ylamino)-2-oxoethyl)triphenylphosphonium chloride (MitoTEMPO), chelerythrine, or forskolin (500, 10, 50, or 5 μM, respectively) applied intracellularly to isolated cardiomyocytes restored the decreased $I_{Na}$ in cardiomyopathic DOCA myocytes;

FIGS. 4D-F illustrate DOCA mice injected with $NAD^+$ or 2-(2,2,6,6-Tetramethylpiperidin-1-oxyl-4-ylamino)-2-oxoethyl)triphenylphosphonium chloride (MitoTEMPO) (100 or 0.7 mg/kg, respectively) showed recovered $I_{Na}$. The minor shifts of $V_{1/2}$ values of steady state gating were not enough to affect the evaluation of the peak currents. * P<0.01 vs sham group;

FIG. 5A illustrates mitochondrial ROS overproduction was observed with DOCA mice myocytes by MitoSOX™ Red (2.9±0.3-fold of sham, P<0.01) in confocal microscopy. DOCA cardiomyocyte treatment with $NAD^+$, 2-(2,2,6,6-Tetramethylpiperidin-1-oxyl-4-ylamino)-2-oxoethyl)triphenylphosphonium chloride (MitoTEMPO), δV1-1, or forskolin (500, 10, 2, or 5 μM, respectively) extracellularly decreased ROS levels in DOCA mouse myocytes to the level of sham group (1.4±0.1, 1.1±0.1, 0.9±0.1, or 0.8±0.1-fold of sham, respectively, P>0.05). Three to five animals were tested in each group, and total 29-43 cells were used for average;

FIG. 5B illustrates DOCA mice injected with $NAD^+$ (100 mg/kg) or 2-(2,2,6,6-Tetramethylpiperidin-1-oxyl-4-ylamino)-2-oxoethyl)triphenylphosphonium chloride (MitoTEMPO) (0.7 mg/kg) showed decreased mitochondrial ROS (1.1±0.1- or 1.1±0.2-fold of sham, respectively, P>0.05). Three to four animals and ~10000 myocytes from each animal were tested in each group in flow cytometry;

FIG. 5C illustrates representative confocal microscopy images from panel A were obtained with treatment of myocytes monitored with MitoTracker™ Green and MitoSOX™ Red. The white scale bar is 20 μm. The extremely red cells are dying myocytes that had very high levels of ROS;

FIG. 6A-D illustrate optical mapping of failing human myocardium;

FIG. 6A illustrates representative left ventricular wedge preparation with key features highlighted. White dotted line—outlines field of view for activation and conduction velocity maps (C and D); blue and green circles—location of optical action potentials (B); pink asterisk—location of pacing stimulus; teal box—boundary of conduction velocity calculation;

FIG. 6B illustrates representative optical action potentials;

FIG. 6C illustrates activation map showing spread of electrical activity across the transmural wedge in 35 ms; and FIG. 6D illustrates: Left panel: Conduction velocity vectors (red) on top of gray scale activation map; center panel: magnification of teal box where conduction velocity calculations were taken; right panel: summary of the conduction velocity of failing hearts before (control) and after treatment (500 μM $NAD^+$) conditions while pacing tissue at several cycle lengths (2000, 1000, 800, 600 ms).

DETAILED DESCRIPTION OF THE PREFERRED EMBODIMENT(S) OF THE INVENTION

Figure 1:
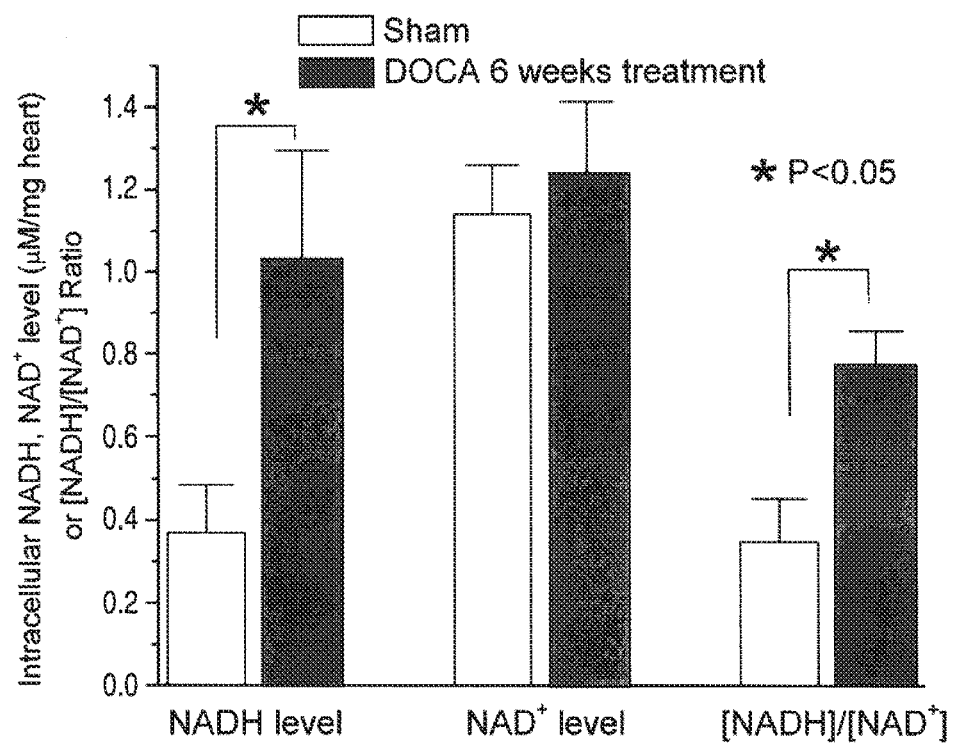
FIG. 1 illustrates intracellular NADH and $NAD^+$ levels and the $[NADH]_i/[NAD^+]_i$ ratio measured in sham and DOCA cardiomyopathic heart tissue. Increased NADH level and $[NADH]_i/[NAD^+]_i$ ratio were seen in DOCA mice.

Cardiomyopathy is associated with cardiac $Na^+$ channel downregulation that may contribute to arrhythmias. Previously, we have shown that elevated intracellular NADH causes a decrease in cardiac Na+ current ($I_{Na}$) signaled by an increase in mitochondrial reactive oxygen species (ROS). Here, we tested whether the NADH-mitochondria ROS pathway was involved in the reduction of $I_{Na}$, in a nonischemic cardiomyopathic model and correlated the findings with myopathic human hearts. We found nonischemic cardiomyopathy was associated with elevated NADH level, PKC activation, mitochondrial ROS overproduction, and a concomitant decrease in $I_{Na}$. Reducing mitochondrial ROS by application of $NAD^+$, 2-(2,2,6,6-Tetramethylpiperidin-1-oxyl-4-ylamino)-2-oxoethyl)triphenylphosphonium chloride (MitoTEMPO), PKC inhibitors, or PKA activators, restored $I_{Na}$, $NAD^+$ improved conduction velocity in human myopathic hearts.

Materials and Methods

Model Generation and Isolation of Mice Ventricular Myocytes

Nonischemic cardiomyopathy was induced in C57BL/6 mice by six weeks of hypertension evoked after unilateral nephrectomy, deoxycorticosterone acetate (DOCA) pellet implantation (0.7 mg/day, Innovative Research of America, Sarasota, Fla.), and 1% salt water substitution (Reference 13). Sham operated mice were used as controls. Ketamine (100 mg/kg) and xylazine (10 mg/kg) were administrated by IP pre-operation and buprenorphine (0.1 mg/kg) was injected subcutaneously post-operation and at 12-hour interval as needed. For each experiment, three to eight mice were used.

Ventricular myocytes were isolated as described before (References 13 and 14). Briefly, hearts were excised from anesthetized mice, perfused with perfusion buffer (in mM: NaCl 113, KCl 4.7, $Na_2HPO_4$ 0.6, $KH_2PO_4$ 0.6, $MgSO_4$ 1.2, Phenol Red 0.032, $NaHCO_3$ 12, $KHCO_3$ 10, HEPES 10, Taurine 30, 2-3-butanedione monoxime 10) and digested with collagenase II (Worthington Biochemical Co. Lakewood, N.J.). Cardiomyocytes were washed with control buffers (in mM: NaCl 133.5, KCl 4, $Na_2HPO_4$ 1.2, HEPES 10, $MgSO_4$ 1.2) with serially increasing $Ca^{2+}$ concentrations (0.2, 0.5, and 1 mM). Then, myocytes were incubated in MEM medium (modified Eagle's medium with 1% insulin-transferrin-selenium, 0.1% bovine serum albumin, 1% L-glutamine, and 1% penicillin/streptomycin) in a 95% $O_2$/5% $CO_2$ incubator at 37° C. for 2 hours prior to being used for patch clamp recording and ROS level measurements.

Documentation of Cardiomyopathy

Blood pressure and heart rate were measured on acclimated conscious mice six weeks after surgery using tail-cuff plethysmography (Columbus Instruments, Columbus, Ohio). Transthoracic echocardiography was performed using the Vevo 770 system equipped with a RMV-707B transducer (VisualSonics, Toronto, Canada). Mice were anesthetized with 1% isoflurane in oxygen and were closely monitored during the procedure. Images were obtained from the parasternal long axis view and parasternal short axis view at the midpapillary level. Wall thickness, chamber size, fractional shortening (% FS), and ejection fraction (% EF) were evaluated by two-dimensional and M-mode echocardiography. Measurements were averaged from three consecutive beats.

Intracellular NADH and $NAD^+$ Levels

Intracellular NADH and $NAD^+$ levels ($[NADH]_i$ and $[NAD^+]_i$) were detected using the EnzyChrom™ $NAD^+$/NADH Assay Kit (BioAssay Systems, Hayward, Calif.) with sham and DOCA mice heart tissue followed the manufacturer's instructions. The intensity difference of the reduced product color, measured at 565 nm at time zero and 15 min later, was used to calculate the change in the concentration of NAD(H).

Cellular Electrophysiology $Na^+$ currents of ventricular myocytes were measured using the whole-cell patch clamp technique in voltage-clamp mode at room temperature (References 9 and 10). To measure $Na^+$ currents, pipettes (1-2 MΩ) were filled with a pipette solution containing (in mM): CsCl 80, cesium aspartate 80, EGTA 11, $MgCl_2$ 1, $CaCl_2$ 1, HEPES 10, and $Na_2ATP$ 5 (adjusted to pH 7.4 with CsOH). The bath solution consisted of (in mM): NaCl 15, CsCl 5, $CaCl_2$ 1, $MgCl_2$ 1, tetramethylammonium Cl 20, N-methyl-D-glucamine 100, 4-aminopyride 3, $MnCl_2$ 2, HEPES 10 and glucose 10 (adjusted to pH 7.4 with CsOH). To measure current, a stepped voltage protocol from −100 to +60 mV with a holding potential of −100 mV was applied to establish the presence of $Na_v1.5$. Peak currents obtained during steps to −20 mV were used for comparison in determining the relative reduction of $I_{Na}$. To minimize time-dependent drift in gating parameters, all protocols were initiated 2-5 min after whole-cell configuration was obtained. The currents were normalized with cell capacitance.

To measure the resting membrane potential, perforated current-clamp was performed on isolated myocytes from sham and DOCA mice (Reference 15). The pipette solution contained (in mM): potassium gluconate 120, KCl 20, NaCl 5, HEPES 5, MgATP 5, and β-escin 0.03 (adjusted to pH 7.2 with KOH). The bath solution consisted of (in mM): NaCl 140, KCl 5.4, $MgCl_2$ 1, HEPES 5, $CaCl_2$ 1.8, and glucose 5.5 (adjusted to pH 7.4 with NaOH). Pipette resistance were 3-5 MΩ.

Measurement of Mitochondrial ROS

To measure mitochondrial ROS, the fluorescent probe MitoSOX™ Red was used according to the manufacturer's protocol. Briefly, ten groups of isolated cardiomyocytes were studied: sham mouse myocytes, DOCA mouse myocytes, and myocytes from sham or DOCA mice treated with 500 μM $NAD^+$, 10 μM 2-(2,2,6,6-Tetramethylpiperidin-1-oxyl-4-ylamino)-2-oxoethyl)triphenylphosphonium chloride (MitoTEMPO), 2 μM δV1-1, or 5 μM forskolin for 10-min at 37° C. Cells were then washed once with MEM and incubated with 5 μM MitoSOX™ Red and 100 nM MitoTracker Green for 10 min at 37° C., followed by washing three times with MEM medium. Images were taken on a Zeiss LSM710 confocal microscope (Carl Zeiss GmbH, Germany) using an argon laser excitation (514 nm) with emission collection through a 560 nm long pass filter. The mean values of the whole cell fluorescence of MitoSOX™ Red were obtained with ImageJ software.

For flow cytometry measurements, isolated cardiomyocytes from sham or DOCA mice injected with 100 mg/kg $NAD^+$ or with 0.7 mg/kg 2-(2,2,6,6-Tetramethylpiperidin-1-oxyl-4-ylamino)-2-oxoethyl)triphenylphosphonium chloride (MitoTEMPO) twice (at 24 h and 1 h before myocyte isolation, respectively) were incubated with MitoSOX™ Red (5 μM) for 15 min and washed twice with MEM. Appropriate gating was used to select cardiomyocytes, and 10,000 cells were read in each sample at FL-2 in CyAN ADP flow cytometry (Beckman-Coulter, Brea, Calif.).

Biotinylation and Western Blotting of $Na_v1.5$

Analysis of $Na^+$ channels present at the cell surface was performed on freshly isolated cardiomyocytes of sham and DOCA mice as previously described with the Pierce® Cell Surface Protein Isolation Kit (Pierce Biotechnology, Rockford, Ill.) (Reference 16). For detection of $Na_v1.5$, the primary antibody (rabbit anti-SCN5A, Alomone Labs, Jerusalem, Israel) was diluted 1:200. Horseradish peroxidase-conjugated goat anti-rabbit IgG secondary antibody (Cell Signaling Technology, Danvers, Mass.) was diluted 1:5000. Actin (Santa Cruz Biotechnology, CA) was used as a loading control.

SCN5A RNA Abundance

Total RNA was isolated (RNeasy Minikit—Qiagen, Valencia, Calif.) from snap frozen ventricular tissue samples taken from sham and DOCA mice (n=3 per group). Equal quantities of total RNA from all samples were used to generate cDNA using the High Capacity cDNA synthesis kit (Applied Biosystems, Carlsbad, Calif.), and quantitative PCR was performed using Fast SYBR green chemistry (Applied Biosystems, Carlsbad, Calif.) on an ABI 7500 platform. Primers were designed against mouse SCN5A (SCN5A_F TTGCTC-CTTCTCTCATGGTTG and SCN5A_R CATGGAGAT-GCTCAAGAAGGA) and Hypoxanthine phosphoribosyl-transferase (HPRT) (HPRT_F AGGCCAGACTTTGTTGGATTT and HPRT_R GGCTTTGTATTTGGCTTTTCC) using Primer3 plus software (http://www.bioinformatics.nl/cgi-bin/primer3plus) and synthesized by MWG (Huntsville, Ala.). HPRT acted as the housekeeping gene by which to normalize SCN5A cDNA. The $2^{-\Delta\Delta Ct}$ method was used for relative quantification between groups. A t-test was used for test for statistical comparison between the two groups.

Conduction Velocity Measurement With Human Failing Heart Tissue

Failing human hearts (n=3) of different cardiomyopathies were provided by Barnes-Jewish Hospital (Washington University in Saint Louis, Mo.) and non-failing donor hearts (n=2) were provided by Mid-America Transplant Services (Saint Louis, Mo.) for comparative purposes. Optical mapping experiments of human hearts were done as previously described (References 17 and 18). Briefly, left ventricular (LV) wedge preparations were isolated from the posterior-lateral LV free wall and perfused through the left marginal artery with Tyrode's solution. Tissue was stained with di-4-ANNEPS (15 μM; Molecular Probes, Eugene, Oreg.) for recording optical action potentials and was immobilized by addition of blebbistatin (10-20 μM; Tocris Bioscience, Ellisville, Mo.) to reduce motion artifact.

Figure 6D:
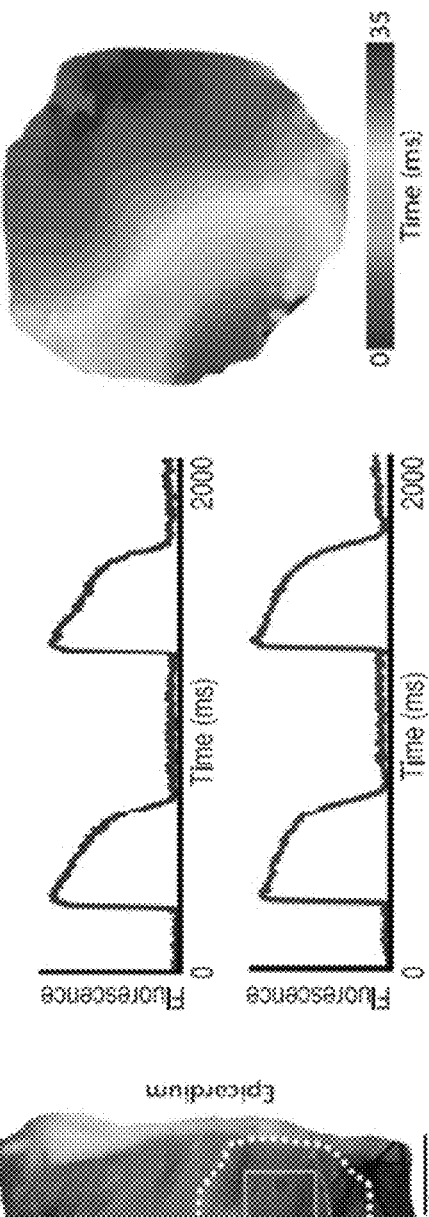
Figure 6D:
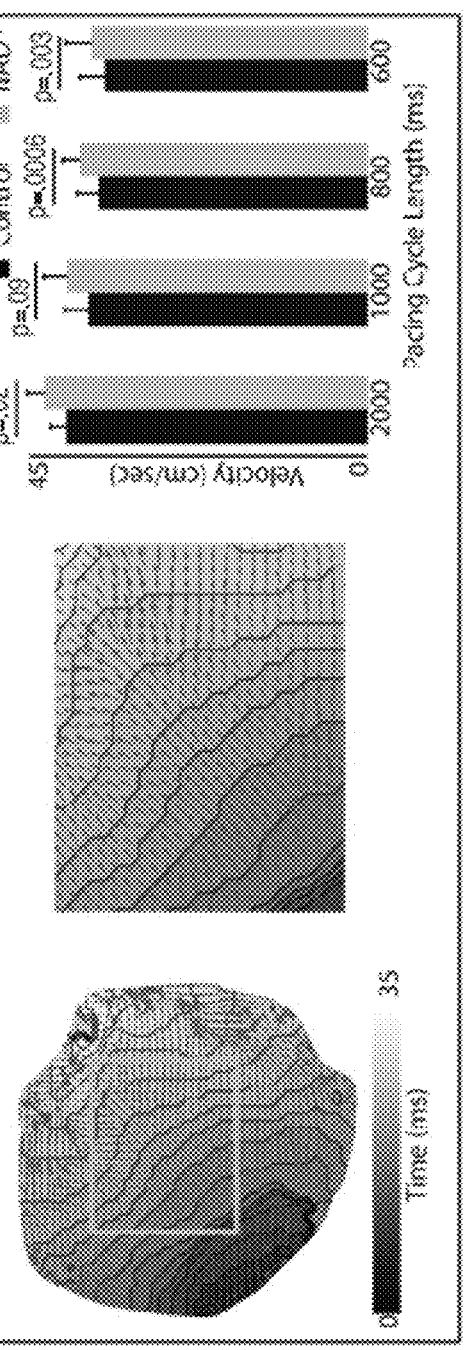

LV wedge preparations were paced at the sub-endocardium at twice the diastolic pacing threshold with a 5-ms pulse width. A restitution pacing protocol was conducted, in which pacing started at 2000 ms and decreased until the ventricular functional refractory period was reached. Following control pacing, $NAD^+$ (500 μM) was bolus-injected into a drug port. Tissue was allowed to stabilize for 25-30 minutes and then a second restitution pacing protocol was performed. Data was analyzed using custom MATLAB software (Reference 19). All optical data were filtered using a 3×3 pixel spatial filter and a 0-100 Hz finite impulse response filter. Activation times were defined as the maximum first derivative of the fluorescent signal and CV was calculated as described by Bayly et al. (Reference 20). The magnitude of CV was determined to be the median conduction calculated in the region of interest (FIG. 6D middle). The Student's paired t-test was used to determine the level of statistical significance ($P<0.05$).

Statistical Evaluations

Data are shown as the mean±SEM. Aside from above, determinations of statistical significance were performed with ANOVA with the Bonferroni correction for comparisons of multiple means. A value of $P<0.05$ was considered statistically significant.

Results

At six weeks after surgery, DOCA mice had developed hypertension and systolic heart dysfunction confirmed by tail-cuff blood pressure measurements and echocardiography. As shown in Table 1 (below), compared to the sham mice, DOCA mice showed higher artery blood pressure, enlarged left ventricular chamber (105±4 vs. 88±6 μL of sham, $P<0.05$), and reduced ejection fraction (37±2% vs. 49±4% of sham, $P<0.05$).

TABLE 1

Blood pressure and Echocardiographic Comparison Between DOCA and Sham Mice

| | Sham | | DOCA | | |
|---|---|---|---|---|---|
| | Value | N | Value | N | P value |
| Heart rate (bpm) | 528 ± 17 | 4 | 533 ± 28 | 5 | NS |
| SBP (mmHg) | 99 ± 7 | 4 | 116 ± 3 | 5 | <0.05 |
| DBP (mmHg) | 74 ± 5 | 4 | 89 ± 3 | 5 | <0.05 |
| LVESV (μL) | 42.1 ± 3.6 | 8 | 64.6 ± 3.3 | 8 | <0.05 |
| LVEDV (μL) | 87.9 ± 6.1 | 8 | 104.7 ± 3.9 | 8 | <0.05 |
| FS (%) | 26.4 ± 1.0 | 8 | 17.9 ± 1.0 | 8 | <0.05 |
| EF (%) | 49.4 ± 3.7 | 8 | 37.1 ± 1.8 | 8 | <0.05 |

Note:
SBP: systolic artery blood pressure;
DBP: diastolic artery blood pressure;
LVESV: left ventricular end-systolic volume;
LVEDV: left ventricular end-diastolic volume;
FS: fractional shortening;
EF: ejection fraction.
Values were compared between DOCA and sham mice at 6 weeks post surgery.
N is the animal number used.

Elevated NADH Level in Cardiomyopathic Heart Tissue

We measured $[NADH]_i$ and $[NAD^+]_i$ of heart tissue of sham and DOCA mice. FIG. 1 shows that the $[NAD^+]_i$ of sham and DOCA groups were similar. On the other hand, $[NADH]_i$ was increased 2.8±0.7-fold in DOCA mice ($P<0.01$ vs. sham). According to our previous work, this amount of increase in intracellular NADH level could lead to significant decrease of $I_{Na}$ (Reference 9). Therefore, we measured the $I_{Na}$ of isolated myocytes of sham and DOCA mice.

Decreased $I_{Na}$ in Cardiomyopathic Ventricular Cardiomyocytes

Figures 2A, 2B:
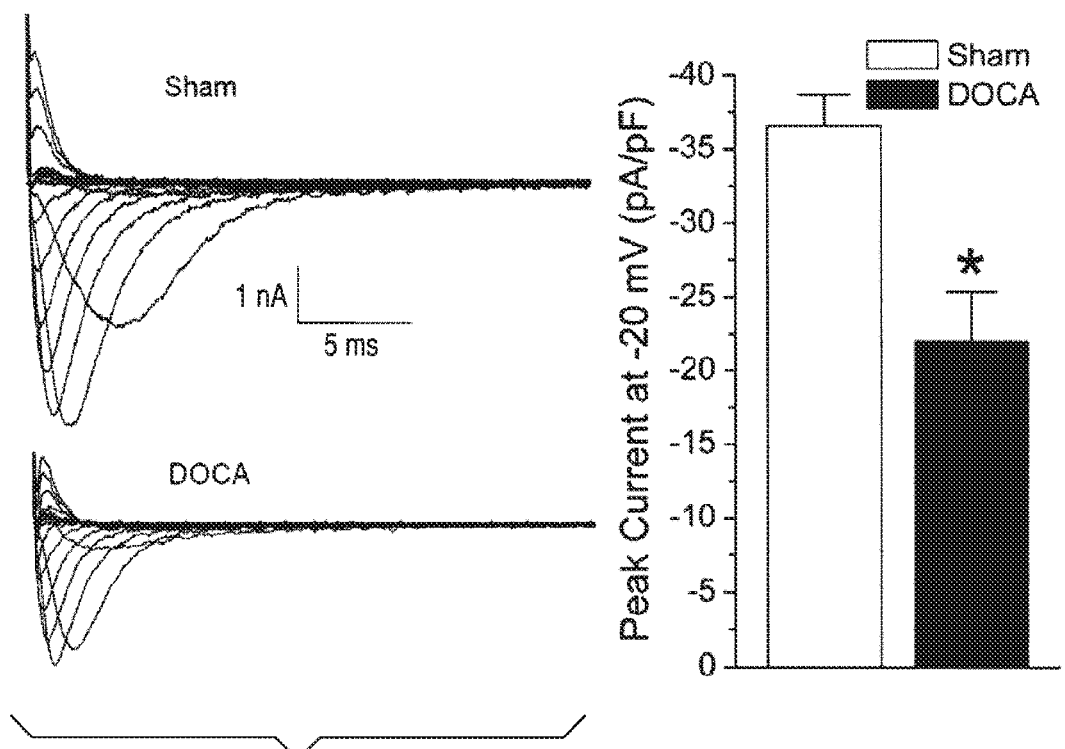
FIGS. 2A-B illustrate that decreased $I_{Na}$ was seen in DOCA cardiomyopathic mice.
Figure 3:
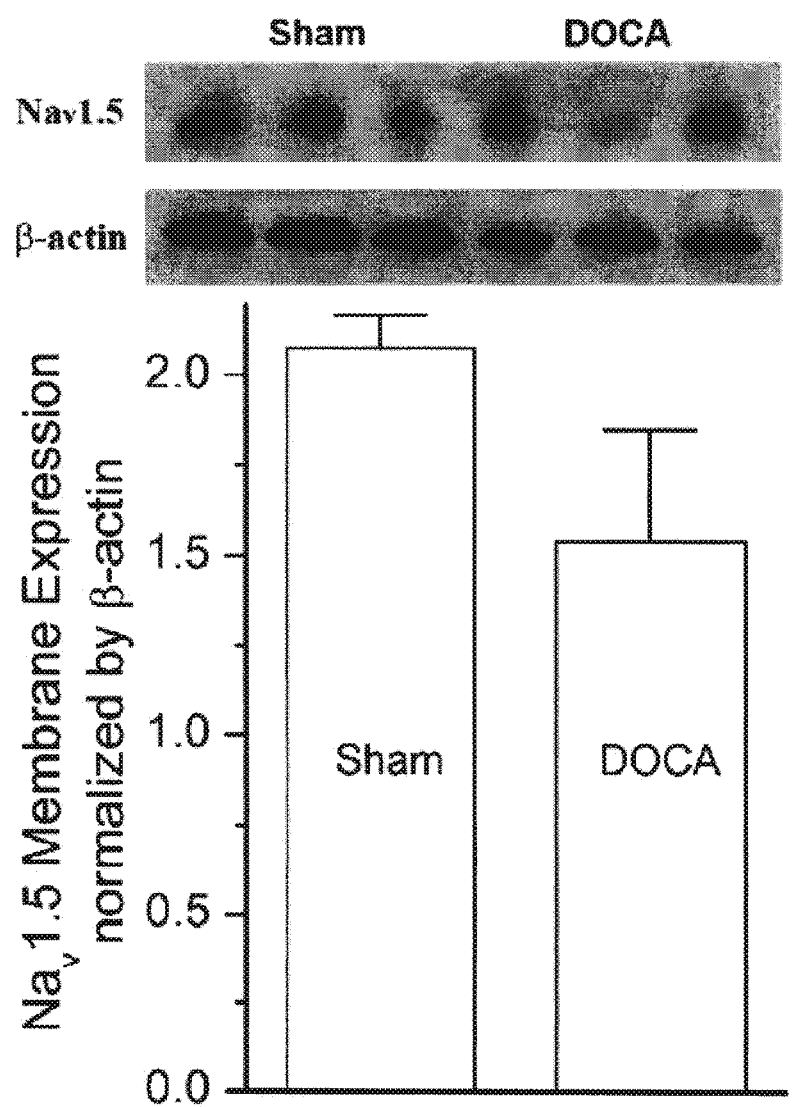
FIG. 3 illustrates $Na_v1.5$ membrane expression measured with biotinylation was unchanged between sham and DOCA mice. In these Western blots, β-actin was used as a loading control. There is no significant change of $Na_v1.5$ protein membrane expressions in DOCA mice cardiomyocytes.

FIG. 2A shows representative traces of $I_{Na}$ measured from isolated sham and DOCA ventricular myocytes. The $I_{Na}$ of DOCA myocytes was significantly decreased. FIG. 2B presents the averaged peak currents measured at −20 mV with a holding potential of −100 mV, $I_{Na}$ of the cardiomyopathy group being 60±10% of the sham ($P<0.01$). The decrease in $I_{Na}$ was not related to changes in transcription, because quantification of SCN5A mRNA revealed no significant difference in transcript levels with the sham and DOCA heart tissue ($P=0.95$). To investigate $Na_v1.5$ membrane expression, we labeled channels present on the membrane surface with biotinylation. Western blot analysis for biotinylated $Na^+$ channels showed no significant difference between sham and DOCA mice as in FIG. 3: 2.07±0.09 vs. 1.54±0.31, n=3 for each group, $P=0.29$. The resting membrane potential of DOCA mice myocytes (−78.3±5.0 mV) was not altered compared to the sham group (−75.5±0.8 mV, $P>0.05$).

Restoring $I_{Na}$

Figure 4A:
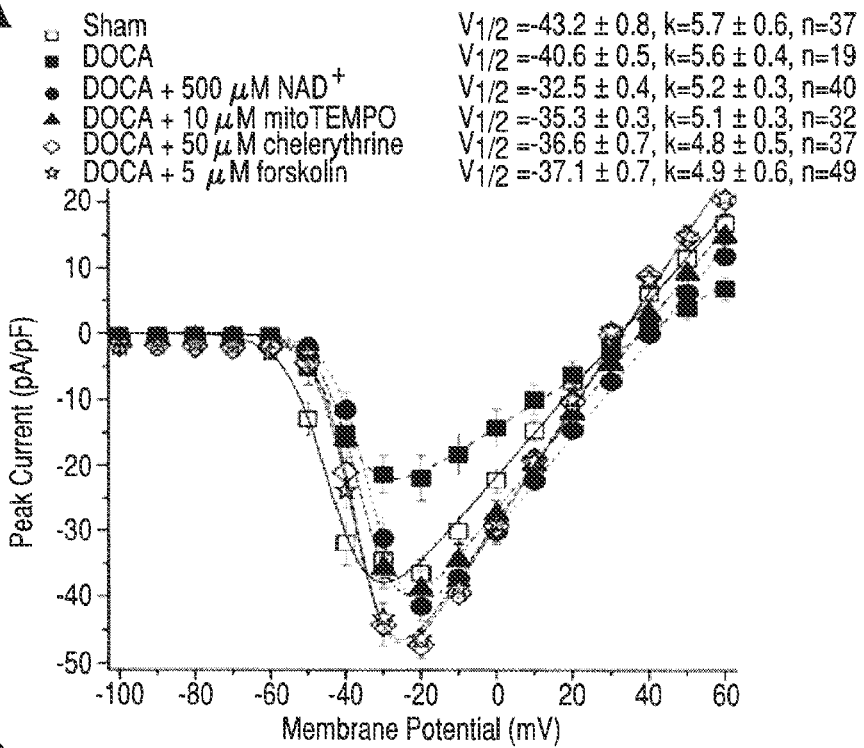
FIGS. 4A-F illustrate reduced $I_{Na}$ in cardiomyopathy was corrected by $NAD^+$ or 2-(2,2,6,6-Tetramethylpiperidin-1-oxyl-4-ylamino)-2-oxoethyl)triphenylphosphonium chloride (MitoTEMPO) without significant changes in channel gating.
Figure 4B:
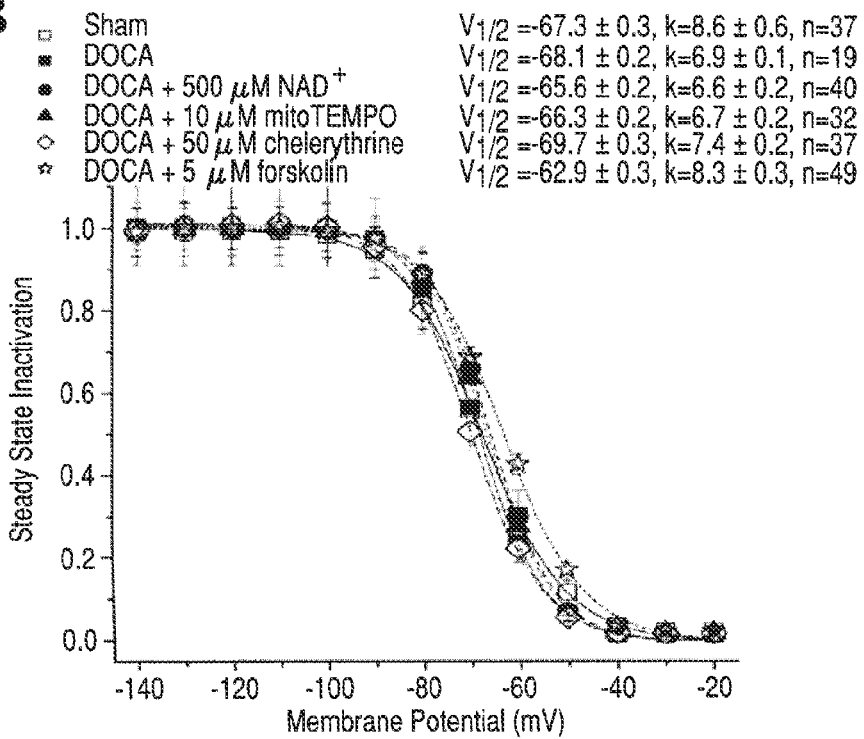
Figure 4C:
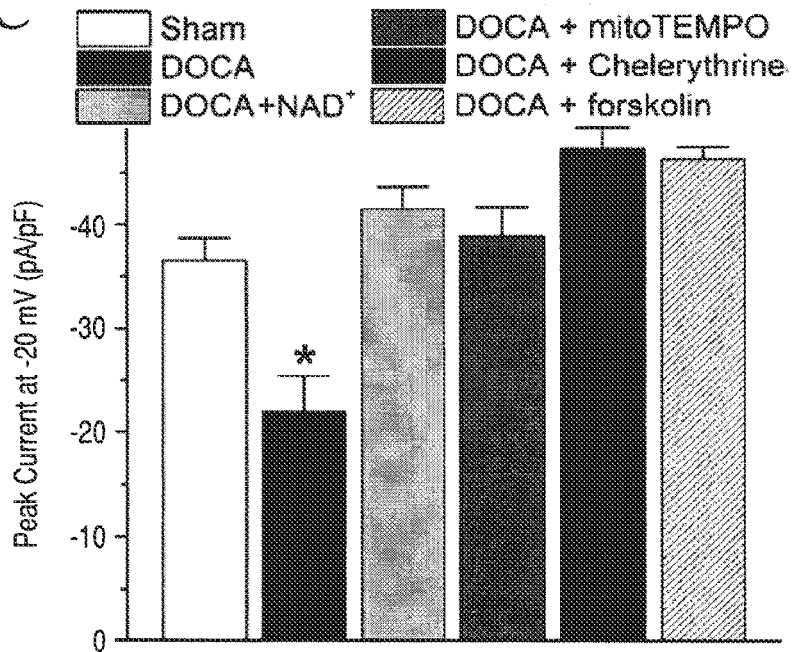

In our previous studies on ventricular cells from normal hearts, $NAD^+$, 2-(2,2,6,6-Tetramethylpiperidin-1-oxyl-4-ylamino)-2-oxoethyl)triphenylphosphonium chloride (MitoTEMPO), chelerythrine and forskolin reversed a NADH-induced decrease of $I_{Na}$ (References 9 and 10). In this work, intracellular application of $NAD^+$, 2-(2,2,6,6-Tetramethylpiperidin-1-oxyl-4-ylamino)-2-oxoethyl)triphenylphosphonium chloride (MitoTEMPO), chelerythrine, or forskolin (500, 10, 50, or 5 μM, respectively) to isolated myocytes of cardiomyopathic mice restored $I_{Na}$ from 60±10% to 97±7%, 93±8%, 112±86%, 109±6% of sham at −20 mV, respectively (FIGS. 4A and 4C, $P>0.05$). As shown in FIGS. 4A and 4B, there were minor shifts of $V_{1/2}$ values of steady state activation and inactivation, but they were not enough to affect the evaluation of the peak currents. Treatment of sham myocytes with these compounds had no influence on $I_{Na}$.

Figure 4D:
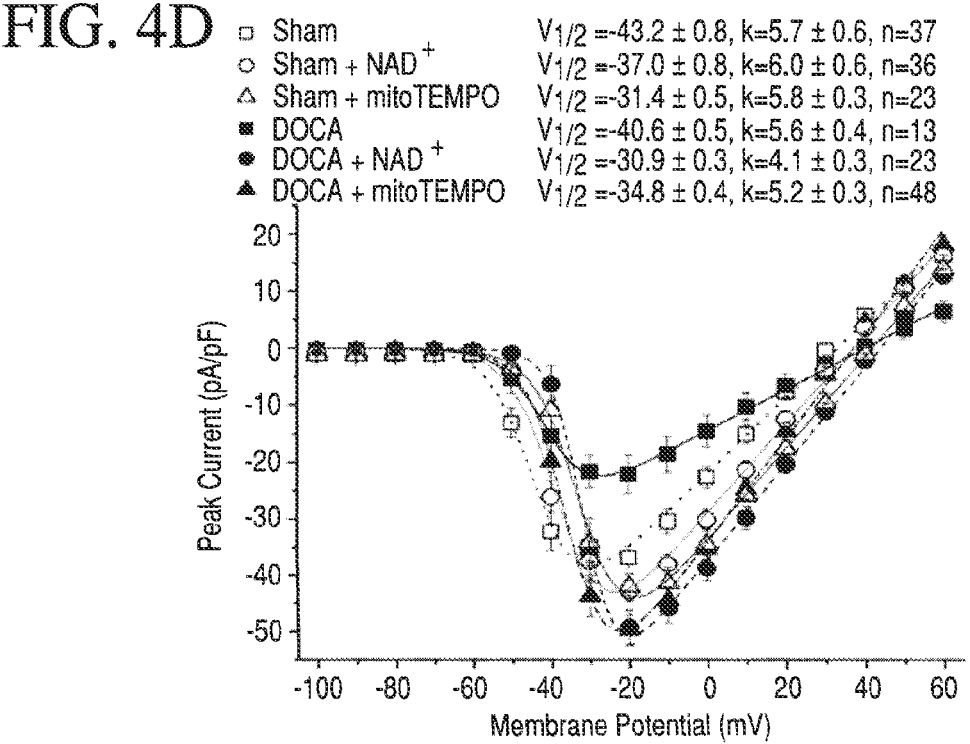
Figure 4E:
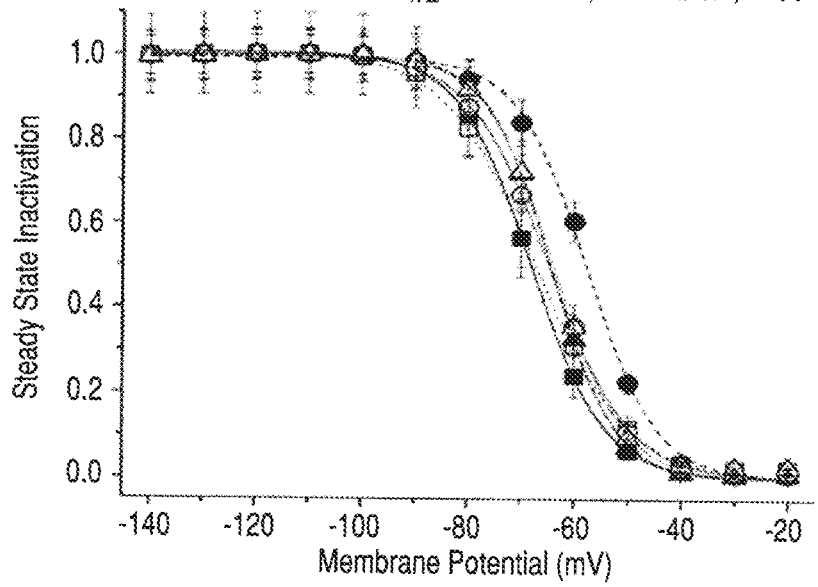
Figure 4F:
Figure 4F:
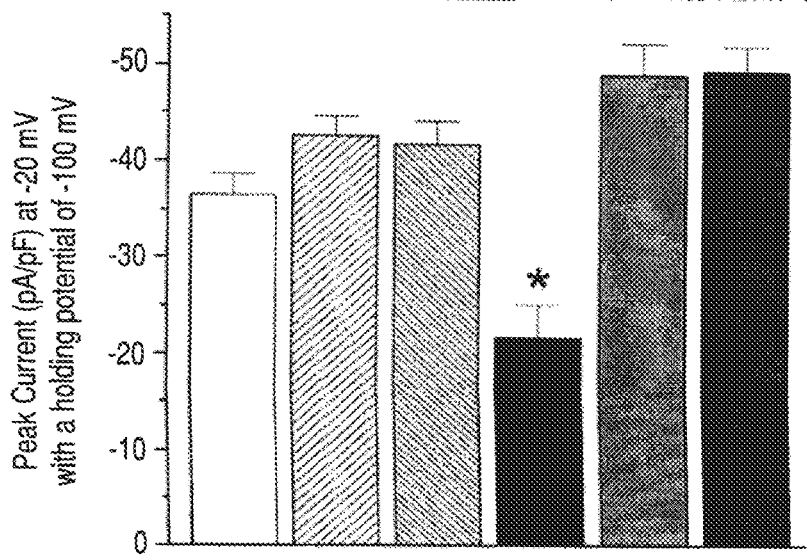

Treating animals with $NAD^+$ and 2-(2,2,6,6-Tetramethylpiperidin-1-oxyl-4-ylamino)-2-oxoethyl)triphenylphosphonium chloride (MitoTEMPO) had similar effects as applying these compounds to isolated myocytes. We injected the animals twice with NAD+ (100 mg/kg) or 2-(2,2,6,6-Tetramethylpiperidin-1-oxyl-4-ylamino)-2-oxoethyl)triphenylphosphonium chloride (MitoTEMPO) (0.7 mg/kg), at 24 hours and 1 hour before the myocyte isolation. As shown in FIGS. 4D and 4F, NAD$^+$ or 2-(2,2,6,6-Tetramethylpiperidin-1-oxyl-4-ylamino)-2-oxoethyl)triphenylphosphonium chloride (MitoTEMPO) completely restored the decreased $I_{Na}$ seen in myopathic myocytes (115±9% and 119±9% of sham injected with NAD$^+$ or 2-(2,2,6,6-Tetramethylpiperidin-1-oxyl-4-ylamino)-2-oxoethyl)triphenylphosphonium chloride (MitoTEMPO), respectively, at −20 mV, P>0.05). As shown in FIGS. 4D and 4E, there were also minor shifts of $V_{1/2}$ values of steady state activation and inactivation that were not enough to affect the evaluation of the peak currents.

Mitochondrial ROS are Increased in Myopathic Ventricular Myocytes

Figure 5A:
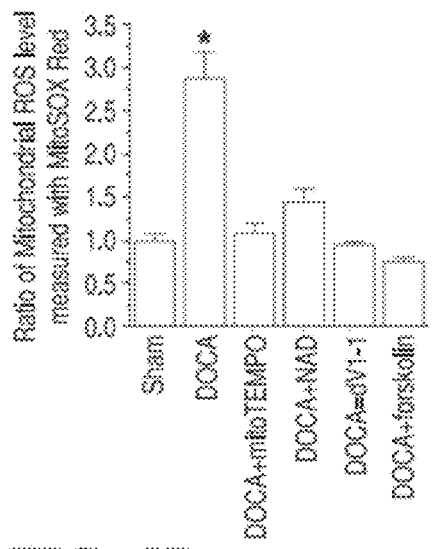
FIGS. 5A-C illustrate mitochondrial ROS levels were increased in DOCA myopathic mice and reduced by $NAD^+$, 2-(2,2,6,6-Tetramethylpiperidin-1-oxyl-4-ylamino)-2-oxoethyl)triphenylphosphonium chloride (MitoTEMPO), δV1-1 and forskolin.

Previously, we have shown that elevated NADH increases mitochondrial ROS production, causing a reduction of Na$^+$ current (References 9 and 10). To test if this mechanism of the $I_{Na}$ reduction was similar in a clinically relevant model, MitoSOX™ Red was used to demonstrate mitochondrial ROS production in myopathic ventricular myocytes of DOCA mice. As shown in FIG. 5A, the mitochondrial ROS level of myopathic myocytes increased ~2.9±0.3-fold (P<0.01 vs. sham). This is similar to a four-fold increase of superoxide production observed in the aortas of DOCA mice (Reference 21).

Figure 5B:
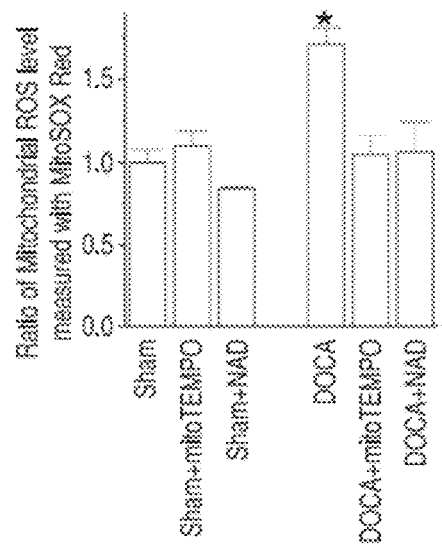
Figure 5C:
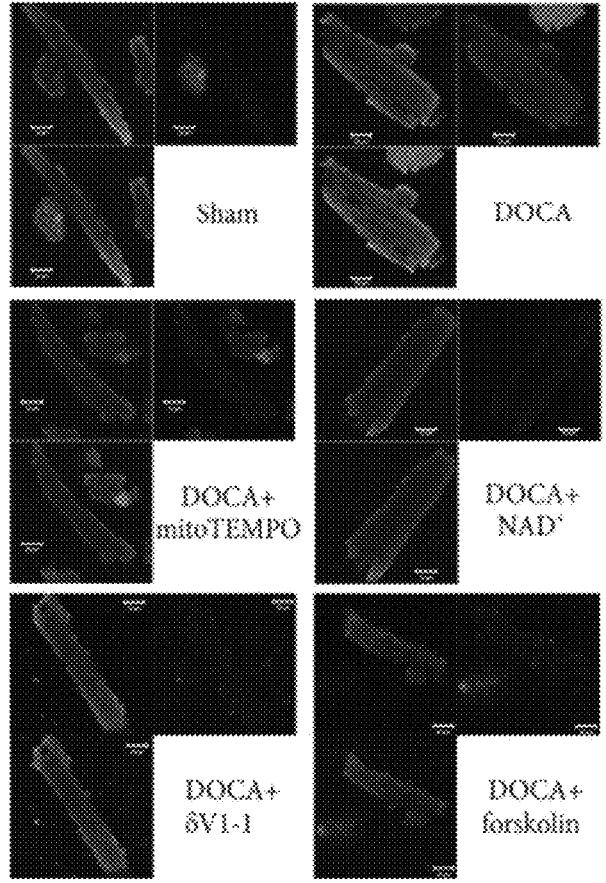

Treatment of myocytes with NAD$^+$, 2-(2,2,6,6-Tetramethylpiperidin-1-oxyl-4-ylamino)-2-oxoethyl)triphenylphosphonium chloride (MitoTEMPO), δV1-1, or forskolin (500, 10, 2, or 5 µM, respectively) extracellularly led to decreases of ROS in myopathic mouse myocytes to levels similar to the sham group (1.4±0.1, 1.1±0.1, 0.9±0.1, or 0.8±0.1-fold of sham, respectively, P>0.05). Here, we used the specific inhibitor of PKCδ, δV1-1, instead of chelerythrine, because chelerythrine's fluorescence affected the evaluation with MitoSOX™ Red. FIG. 5C shows representative confocal images of these measurements. Treatment of sham myocytes with these compounds had no effect on mitochondrial ROS production. For the animal treated groups, we used flow cytometry to test the MitoSOX™ Red fluorescence. This method measured ~10,000 myocytes for each group to produce more reliable measure of net mitochondrial ROS. Similar results to those with confocal microscopy were obtained with sham, DOCA and DOCA mice injected with NAD+ or 2-(2,2,6,6-Tetramethylpiperidin-1-oxyl-4-ylamino)-2-oxoethyl)triphenylphosphonium chloride (MitoTEMPO) (100 or 0.7 mg/kg, respectively; FIG. 5B). The mean fluorescent intensity of the myopathic DOCA group was increased by 1.7±0.1-fold when compared to sham (P<0.05). NAD+ and 2-(2,2,6,6-Tetramethylpiperidin-1-oxyl-4-ylamino)-2-oxoethyl)triphenylphosphonium chloride (MitoTEMPO) decreased the mitochondrial ROS overproduction in myopathic mouse myocytes to 1.1±0.2- and 1.0±0.1-fold of sham, respectively (P>0.05).

NAD$^+$ Improved the Conduction Velocity of Human Failing Hearts

We tested the clinical relevance of the DOCA mouse model findings in isolated human heart tissue. CV from non-failing and failing hearts were similar to what has been previously reported (Reference 22). Failing hearts showed a reduction in CV that improved with NAD$^+$. For both failing (n=3) and non-failing (n=2) human hearts, CV was calculated both before and after administration of NAD$^+$ at several pacing cycle lengths (2000, 1000, 800, 600 ms). FIG. 6A shows a representative LV wedge preparation with key features highlighted. The dotted white line indicates the field of view of activation and CV maps (FIGS. 6C and 6D left), where the CV was calculated within the teal rectangle. Blue and green circles in FIG. 6A specify the location of representative optical action potentials seen in FIG. 6B. The activation map in FIG. 6C depicts the spread of electrical propagation from the location of the pacing electrode near the sub-endocardium (blue) to the epicardial surface (red).

In FIG. 6D, CV vectors (red arrows) are displayed on top of an activation map in gray scale. The center panel magnifies the area (teal box) where the magnitude of CV was determined at all cycle lengths (2000, 1000, 800, 600 ms) for individual wedge preparations. The mean values of CV of failing hearts and control hearts before and after administration of NAD+ are listed in Table 2 (below). After addition of NAD$^+$, the CV of failing heart increased at all cycle lengths and was significantly different at three cycle lengths (2000 ms: P=0.02, 800 ms: P=0.0006, and 600 ms: P=0.003).

TABLE 2

The Mean Values of Conduction Velocity (cm/s) of Human Failing and Normal Heart Before and After NAD$^+$ Treatment

| | Pacing Cycle Length (ms) | | | |
|---|---|---|---|---|
| | 2000 | 1000 | 800 | 600 |
| Control heart | 49.2 ± 0.2 | 47.4 ± 0.7 | 51.7 ± 0.6 | 47.1 ± 4.5 |
| Control heart + NAD$^+$ | 47.4 ± 0.7 | 47.2 ± 1.4 | 46.7 ± 1.9 | 47.5 ± 3.1 |
| Failing heart | 38.7 ± 2.1 | 35.8 ± 3.1 | 34.6 ± 2.8 | 33.8 ± 3.2 |
| Failing heart + NAD$^+$ | 41.5 ± 2.2* | 38.6 ± 3.0 | 37.0 ± 2.3* | 35.5 ± 3.3* |
| Ratio of Failing/Control | 0.79 ± 0.04 | 0.76 ± 0.07 | 0.67 ± 0.05 | 0.72 ± 0.1 |
| Ratio of Failing + NAD$^+$/Failing | 1.07 ± 0.08 | 1.08 ± 0.13 | 1.07 ± 0.11 | 1.05 ± 0.14 |

Note:
*P < 0.05 vs failing heart group.

Discussion

Voltage-gated Na$^+$ channels are responsible for generating the main current for excitation propagation in the membrane of most excitable cells, such as cardiomyocytes and neurons (References 23 and 24). Cardiac Na$^+$ channel changes have been implicated in the increased risk of sudden death in heart failure (References 25-27). In our previous studies on the mechanism by which mutations in glycerol-3-phosphate dehydrogenase 1 like (GPD1L) protein cause reduced $I_{Na}$, and Brugada Syndrome, we have shown that increased NADH can downregulate the cardiac Na$^+$ channel through PKC activation and mitochondrial ROS overproduction (References 9 and 10). Here, we demonstrated that the metabolic derangements occurring in cardiomyopathy resulted in reductions in $I_{Na}$ by a similar mechanism. Hypertensive DOCA mice presented enlarged left ventricular chamber and reduced ejection fraction associated with elevated intracellular NADH level, increased mitochondrial ROS, and reduced $I_{Na}$. The reduction in $I_{Na}$ was on the order of magnitude seen in Brugada Syndrome. These results reveal links between mitochondrial dysfunction with ROS overproduction, downregulation of cardiac Na$_v$1.5, and nonischemic cardiomyopathy. The heart tissue of DOCA mice showed no change in SCN5A mRNA abundance or Na$_v$1.5 protein membrane expression. The reason for decreased $I_{Na}$ is, therefore, not a decrease of Na$_v$1.5 channel number, but decreases of the probability of channel opening or of the single channel conductance. The increase in cardiac mitochondrial ROS is consistent with other studies showing that DOCA-salt treatment increases ROS production in the aorta of DOCA hypertension mice (References 13 and 21) and rats (References 28 and 29).

The improved CV of human failing heart by administration of NAD$^+$ was consistent with the changes in $I_{Na}$ seen in the DOCA mouse model based on the cable equation, where the CV is proportional to $I_N^{1/8}$. The ratio of CV of the failing hearts versus NAD$^+$-treated failing hearts is 1.05-1.08 at pacing cycle lengths of 600-2000 ms. This is in range of improvement in CV calculated for the changes in $I_{Na}$ observed in the DOCA mouse myocytes with NAD$^+$ treatment (i.e. 1.08). Despite the consistency with the mouse model and the likely salutary nature of improving conduction, we cannot rule out that NAD$^+$ had other effects that improved CV aside from increasing $I_{Na}$.

In the study of the GPD1L A280V mutant, NAD$^+$ and 2-(2,2,6,6-Tetramethylpiperidin-1-oxyl-4-ylamino)-2-oxoethyl)triphenylphosphonium chloride (MitoTEMPO) were able to reverse the phenotype and reduce spontaneously induced arrhythmias in a mouse model of Brugada Syndrome (Reference 9). Here, we found that these compounds had analogous effects to raise $I_{Na}$ in the nonischemic cardiomyopathy DOCA model. Treating either myocytes directly or the animal, NAD$^+$ and 2-(2,2,6,6-Tetramethylpiperidin-1-oxyl-4-ylamino)-2-oxoethyl)triphenylphosphonium chloride (MitoTEMPO) were able to reduce mitochondrial ROS overproduction and rectify the decreased $I_{Na}$. This suggests that while there may be other sources of oxidative stress in this cardiomyopathy model, mitochondrial ROS are most important for the reduction in $I_{Na}$. Interestingly, 2-(2,2,6,6-Tetramethylpiperidin-1-oxyl-4-ylamino)-2-oxoethyl)triphenylphosphonium chloride (MitoTEMPO) has also been tested in DOCA mice that show hypertension and resulted in reduced blood pressure (Reference 30).

We examined the involvement of PKA and PKC in the reduction of $I_{Na}$ and overproduction of mitochondrial ROS in DOCA mouse myocytes with forskolin, chelerythrine, and δV1-1. They enhanced $I_{Na}$ and blunted the elevated mitochondrial ROS level of DOCA mouse myocytes. This indicates that, similar to the mechanism we have found in the mutant A280V GDP1L modulation of the cardiac $Na_v1.5$ (References 9 and 10), PKC activation participates in the signaling pathway decreasing the $I_{Na}$ in DOCA mice myocytes, and that PKA activation can be used to upregulate cardiomyocyte $Na_v1.5$ of DOCA mice by inhibiting mitochondrial ROS overproduction. In a study of the vertebrate brain type IIA Na$^+$ channel expressed in *Xenopus oocytes* on single channel level, the open time constant decreased from 0.26±0.05 ms to 0.17±0.03 ms with treatment of 5 nM phorbol 12-myristate 13-acetate (PMA, a PKC activator) at −50 mV (Reference 31). Treatment of PMA also led to a reduced peak Na$^+$ current, reduced channel open probability, and prolonged time constants for channel activation. A reduction in $I_{Na}$ secondary to changes in channel gating is consistent with our observations that $Na_v1.5$ mRNA and membrane protein were unchanged with cardiomyopathy or treatment.

Mitochondria comprise ~30-40% of the myocyte volume, generate >90% of the ATP (References 32, 33), and play a key role in many cellular functions including energy production, ion homeostasis, and cell signaling of cardiomyocytes. Mitochondria are one of the major sources of ROS in heart disease (Reference 34). It is not surprising to find that mitochondrial dysfunction plays a critical role in nonischemic cardiomyopathy. Mitochondrial dysfunction can result in overproduction of ROS, acute energy failure, and cell death (Reference 35). For example, a study of canine heart failure showed a decrease in the enzymatic activity of the complex I of the mitochondrial electron transport chain in heart failure, which caused the functional uncoupling of the respiratory chain and ROS overproduction (Reference 36). In ischemia/reperfusion injury, the complex I serves as the source of ROS (Reference 37). Mitochondrial injury occurring in ischemia is associated with increased NADH and ROS levels (References 11 and 12).

It is unclear whether ROS participates directly in channel regulation or a second messenger pathway. The most vulnerable target of the posttranslational redox modifications to proteins is protein cysteine thiols, the oxidation of which may result in reversible molecular disulfide formation or other thiol modications such as nitrosylation and glutathiolation (References 38-41). In this study of the nonischemic cardiomyopathy model of 6-week DOCA mice, we observed a ~3-fold of mitochondrial ROS overproduction, which participated in the downregulation of cardiac $Na_v1.5$ function in an unknown mechanism. The specific mitochondrial ROS scavenger, 2-(2,2,6,6-Tetramethylpiperidin-1-oxyl-4-ylamino)-2-oxoethyl)triphenylphosphonium chloride (MitoTEMPO) curbed the mitochondrial ROS formation and reinstated $I_{Na}$ to the level of sham mice. PKC inhibitors, chelerythrine and δV1-1, were able to diminish the overproduction of mitochondrial ROS and restore the decreased $I_{Na}$ of DOCA mouse myocytes, indicating that mitochondrial ROS generation is regulated by PKC in this cardiomyopathy heart model. NAD$^+$ and forskolin showed similar regulations on the mitochondrial ROS and $I_{Na}$ levels of DOCA mouse myocytes as PKC inhibitors. On the other hand, both PKC and PKA-mediated phosphorylation has been shown to regulate the channel directly (References 42 and 43). It is possible that these kinases are both up and downstream of mitochondrial ROS production or that ROS-dependent modifications and phosphorylation interact at the channel to modulate current. Further experiments will be needed to differentiate these possibilities.

It is well recognized that increasing severity of myopathy parallels sudden death risk (Reference 44) and reduced $I_{Na}$ increases arrhythmic risk (Reference 45). These studies suggest that myopathy is linked directly to reduced $I_{Na}$ and describe a mechanism whereby myopathy leads to metabolic derangements and increased mitochondrial ROS production causing the reduced $I_{Na}$. This work suggests a reduction in mitochondrial ROS in cardiomyopathy will reverse the reduced $I_{Na}$ and possibly some of the arrhythmic risk by improving conduction velocity.

While this invention has been described as having preferred sequences, ranges, steps, materials, structures, components, features, and/or designs, it is understood that it is capable of further modifications, uses, and/or adaptations of the invention following in general the principle of the invention, and including such departures from the present disclosure as those come within the known or customary practice in the art to which the invention pertains, and as may be applied to the central features hereinbeforesetforth, and fall within the scope of the invention and of the limits of the appended claims.

REFERENCES

The following references, including those cited in the disclosure herein, are hereby incorporated herein in their entirety by reference.

[1] Bardy G H, Lee K L, Mark D B, Poole J E, Packer D L, Boineau R et al. Amiodarone or an implantable cardioverter-defibrillator for congestive heart failure. N Engl J Med 2005; 352:225-37.

[2] Kamphuis H C M, de Leeuw J R J, Derksen R, Hauer R N W, Winnubst J A M. Implantable cardioverter defibrillator recipients: quality of life in recipients with and without ICD shock delivery. Europace 2003; 5:381-9.

[3] Thomas S A, Friedmann E, Kao C W, Inguito P, Metcalf M, Kelley F J et al. Quality of life and psychological status of patients withiImplantable cardioverter defibrillators. Am J Crit Care 2006; 15:389-98.

[4] Valdivia C R, Chu W W, Pu J, Foell J D, Haworth R A, Wolff M R et al. Increased late sodium current in myocytes from a canine heart failure model and from failing human heart. J Mol Cell Cardiol 2005; 38:475-83.

[5] Ufret-Vincenty C A, Baro D J, Lederer W J, Rockman H A, Quinones L E, Santana L F. Role of sodium channel deglycosylation in the genesis of cardiac arrhythmias in heart failure. J Biol Chem 2001; 276:28197-203.

[6] Pu J, Boyden P A. Alterations of Na+ currents in myocytes from epicardial border zone of the infarcted heart. A possible ionic mechanism for reduced excitability and postrepolarization refractoriness. Circ Res 1997; 81:110-9.

[7] Baba S, Dun W, Boyden P A. Can PKA activators rescue Na+ channel function in epicardial border zone cells that survive in the infarcted canine heart? Cardiovasc Res 2004; 64:260-7.

[8] Shaw R M, Rudy Y. Ionic mechanisms of propagation in cardiac tissue: roles of the sodium and L-type calcium currents during reduced excitability and decreased gap junction coupling. Circ Res 1997; 81:727-41.

[9] Liu M, Sanyal S, Gao G, Gurung I S, Zhu X, Gaconnet G et al. Cardiac Na+ current regulation by pyridine nucleotides. Circ Res 2009; 105:737-45.

[10] Liu M, Liu H, Dudley S C, Jr. Reactive oxygen species originating from mitochondria regulate the cardiac sodium channel. Circ Res 2010; 107:967-74.

[11] Aon M A, Cortassa S, Marban E, O'Rourke B. Synchronized whole cell oscillations in mitochondrial metabolism triggered by a local release of reactive oxygen species in cardiac myocytes. J Biol Chem 2003; 278:44735-44.

[12] Di L F, Menabo R, Canton M, Barile M, Bernardi P. Opening of the mitochondrial permeability transition pore causes depletion of mitochondrial and cytosolic NAD+ and is a causative event in the death of myocytes in postischemic reperfusion of the heart. J Biol Chem 2001; 276:2571-5.

[13] Silberman G A, Fan T-H, Liu H, Jiao Z, Xiao H D, Lovelock J D et al. Uncoupled cardiac nitric oxide synthase mediates diastolic dysfunction. Circulation 2010; 121:519-28.

[14] O'Connor D T, Rodrigo M, Simpson P. Isolation and culture of adult mouse cardiac myocytes. Methods Mol Biol 2007; 357:271-96.

[15] Bogdanov K Y, Vinogradova T M, Lakatta E G. Sinoatrial nodal cell ryanodine ceceptor and Na+-Ca2+ exchanger:molecular partners in pacemaker regulation. Circ Res 2001; 88:1254-8.

[16] London B, Michalec M, Mehdi H, Zhu X, Kerchner L, Sanyal S et al. Mutation in Glycerol-3-Phosphate Dehydrogenase 1-Like Gene (GPD1-L) Decreases Cardiac Na+ Current and Causes Inherited Arrhythmias. Circulation 2007; 116:2260-8.

[17] Lou Q, Fedorov V V, Glukhov A V, Moazami N, Fast V G, Efimov I R. Transmural heterogeneity and remodeling of ventricular excitation-contraction coupling in human heart failure/clinical perspective. Circulation 2011; 123:1881-90.

[18] Fedorov V V, Glukhov A V, Ambrosi C M, Kostecki G, Chang R, Janks D et al. Effects of KATP channel openers diazoxide and pinacidil in coronary-perfused atria and ventricles from failing and non-failing human hearts. J Mol Cell Cardiol 2011; 51:215-25.

[19] Laughner J I, Sulkin M S, Wu Z, Deng C X, Efimov I R. Three potential mechanisms for failure of high intensity focused ultrasound ablation in cardiac tissue/clinical perspective. Circ: Arrhythm Electrophysiol 2012; 5:409-16.

[20] Bayly P, KenKnight B, Rogers J, Hillsley R, Ideker R, Smith W. Estimation of conduction velocity vector fields from epicardial mapping data. IEEE Trans Biomed Eng 1998; 45:563-71.

[21] Landmesser U, Dikalov S, Price S R, McCann L, Fukai T, Holland S et al. Oxidation of tetrahydrobiopterin leads to uncoupling of endothelial cell nitric oxide synthase in hypertension. J Clin Invest 2003; 111:1201-9.

[22] Glukhov A V, Fedorov V V, Kalish P W, Ravikumar V K, Lou Q, Janks D et al. Conduction remodeling in human end-stage nonischemic left ventricular cardiomyopathy/clinical perspective. Circulation 2012; 125:1835-47.

[23] Abriel H. Cardiac sodium channel Nav1.5 and its associated proteins. Arch Mal Coeur Vaiss 2007; 100:787-93.

[24] Shibata E F, Brown T L, Washburn Z W, Bai J, Revak T J, Butters C A. Autonomic regulation of voltage-gated cardiac ion channels. J Cardiovasc Electrophysiol 2006; 17 Suppl 1:S34-S42.

[25] Akai J, Makita N, Sakurada H, Shirai N, Ueda K, Kitabatake A et al. A novel SCN5A mutation associated with idiopathic ventricular fibrillation without typical ECG findings of Brugada syndrome. FEBS Lett 2000; 479:29-34.

[26] Brugada P, Brugada R, Brugada J. The Brugada syndrome. Curr Cardiol Rep 2000; 2:507-14.

[27] Makiyama T, Akao M, Tsuji K, Doi T, Ohno S, Takenaka K et al. High risk for bradyarrhythmic complications in patients with Brugada syndrome caused by SCN5A gene mutations. J Am Coll Cardiol 2005; 46:2100-6.

[28] Beswick R A, Zhang H, Marable D, Catravas J D, Hill W D, Webb R C. Long-term antioxidant administration attenuates mineralocorticoid hypertension and renal inflammatory response. Hypertension 2001; 37:781-6.

[29] Beswick R A, Dorrance A M, Leite R, Webb R C. NADH/NADPH oxidase and enhanced superoxide production in the mineralocorticoid hypertensive rat. Hypertension 2001; 38:1107-11.

[30] Dikalova A E, Bikineyeva A T, Budzyn K, Nazarewicz R R, McCann L, Lewis W et al. Therapeutic targeting of mitochondrial superoxide in hypertension. Circ Res 2010; 107:106-16.

[31] Schreibmayer W, Dascal N, Lotan I, Wallner M, Weigl L. Molecular mechanism of protein kinase C modulation of sodium channel α-subunits expressed in *Xenopus oocytes*. FEBS Lett 1991; 291:341-4.

[32] Murphy E, Steenbergen C. Preconditioning: the mitochondrial connection. Annu Rev Physiol 2007; 69:51-67.

[33] Barth E, Stammler G, Speiser B, Schaper J. Ultrastructural quantitation of mitochondria and myofilaments in cardiac muscle from 10 different animal species including man. J Mol Cell Cardiol 1992; 24:669-81.

[34] Das D K, Maulik N. Mitochondrial function in cardiomyocytes: target for cardioprotection. Curr Opin Anaesthesiol 2005; 18:77-82.

[35] Duchen M R. Contributions of mitochondria to animal physiology: from homeostatic sensor to calcium signalling and cell death. J Physiol 1999; 516:1-17.

[36] Ide T, Tsutsui H, Kinugawa S, Utsumi H, Kang D, Hattori N et al. Mitochondrial electron transport complex I is a potential source of oxygen free radicals in the failing myocardium. Circ Res 1999; 85:357-63.

[37] Andrukhiv A, Costa ADT, West I, Garlid K D. Opening mitoKATP increases superoxide generation from complex I of the electron transport chain. Am J Physiol Heart Circ Physiol 2006; 291:H2067-H2074.

[38] Eaton P. Protein thiol oxidation in health and disease: techniques for measuring disulfides and related modifications in complex protein mixtures. Free Radic Biol Med 2006; 40:1889-99.

[39] Winterbourn C C. Reconciling the chemistry and biology of reactive oxygen species. Nat Chem Biol 2008; 4:278-86.

[40] Santos C X C, Anilkumar N, Zhang M, Brewer A C, Shah A M. Redox signaling in cardiac myocytes. Free Radic Biol Med 2011; 50:777-93.

[41] Lovelock J D, Monasky M M, Jeong E M, Lardin H A, Liu H, Patel B G et al. Ranolazine improves cardiac diastolic dysfunction through modulation of myofilament calcium sensitivity. Circ Res 2012; 110:841-50.

[42] Zhou J, Shin H G, Yi J, Shen W, Williams C P, Murray K T. Phosphorylation and putative ER retention signals are required for protein kinase A-mediated potentiation of cardiac sodium current. Circ Res 2002; 91:540-6.

[43] Tateyama M, Kurokawa J, Terrenoire C, Rivolta I, Kass R S. Stimulation of protein kinase C inhibits bursting in disease-linked mutant human cardiac sodium channels. Circulation 2003; 107:3216-22.

[44] Epstein A E, DiMarco J P, Ellenbogen K A, Estes III N A M, Freedman R A, Gettes L S et al. ACC/AHA/HRS 2008 guidelines for device-based therapy of cardiac rhythm abnormalities: a report of the American College of Cardiology/American Heart Association Task Force on practice guidelines (writing committee to revise the ACC/AHA/NASPE 2002 guideline update for implantation of cardiac pacemakers and antiarrhythmia devices) developed in collaboration with the American Association for Thoracic Surgery and Society of Thoracic Surgeons. J Am Coll Cardiol 2008; 117: e350-e408.

[45] Ruan Y, Liu N, Priori S G. Sodium channel mutations and arrhythmias. Nat Rev Cardiol 2009; 6:337-48.

[46] Abriel H, Kass R S. Regulation of the voltage-gated cardiac sodium channel $Na_v1.5$ by interacting proteins. Trends Cardiovasc Med 2005; 15(1):35-40.

[47] Zicha S, Maltsev V A, Nattel S, Sabbah H N, Undrovinas A I. Post-transcriptional alterations in the expression of cardiac $Na^+$ channel subunits in chronic heart failure. J Mol Cell Cardiol 2004; 37(1):91-100.

[48] Bruzzone S, Moreschi I, Guida L, Usai C, Zocchi E, De-aflora A. Extracellular $NAD^+$ regulates intracellular calcium levels and induces activation of human granulocytes. Biochem J 2006; 393(3):697-704.

[49] Romanello M, Padoan M, Franco L, Veronesi V, Moro L, D'Andrea P. Extracellular $NAD^+$ induces calcium signaling and apoptosis in human osteoblastic cells. Biochem Biophys Res Commun 2001; 285(5):1226-31.

[50] Bobalova J, Mutafova-Yambolieva V N. Activation of the adenylyl cyclase/protein kinase A pathway facilitates neural release of β-nicotinamide adenine dinucleotide in canine mesenteric artery. Eur J Pharmacol 2006; 536(1-2):128-32.

[51] Technikova-Dobrova Z, Sardanelli A, Speranza F, Scacco S, Signorile A, Lorusso V, Papa S. Cyclic adenosine monophosphate-dependent phosphorylation of mammalian mitochondrial proteins: enzyme and substrate characterization and functional role. Biochemistry 2010; 40:13941-7.

[52] Xie G H, Rah S Y, Kim S J, Nam T S, Ha K C, Chae S W, Im M J, Kim U H. ADP-ribosyl cyclase couples to cyclic AMP signaling in the cardio myocytes. Biochem Biophys Res Commun 2005; 330 (4):1290-8.

[53] Zhang F, Jin S, Yi F, Xia M, Dewey W L, Li P L. Local production of $O_2^-$ by NAD(P)H oxidase in the sarcoplasmic reticulum of coronary arterial myocytes: cADPR-mediated $Ca^{2+}$ regulation. Cell Signal 2008; 20(4):637-44.

[54] Deng N, Zhang J, Zong C, Wang Y, Lu H, Yang P, Wang W, Young G W, Wang Y, Korge P, Lotz C, Doran P, Liem D A, Apweiler R, Weiss J N, Duan H, Ping P. Phosphoproteome analysis reveals regulatory sites in major pathways of cardiac mitochondria. Mol Cell Proteomics 2011; 10(2): M110.000117.

[55] Kohlhaas M, Liu T, Knopp A, Zeller T, Ong M F, Bohm M, O'Rourke B, Maack C. Elevated cytosolic $Na^+$ increases mitochondrial formation of reactive oxygen species in failing cardiac myocytes. Circulation 2010; 121 (14):1606-13.

What is claimed is:

1. A method of reducing arrhythmic risk in an individual with cardiomyopathy characterized by an enlarged chamber and reduced conduction velocity, comprising the steps of:
   a) providing an individual with said cardiomyopathy and reduced conduction velocity;
   b) improving the conduction velocity to a predetermined normal by administering to the individual a therapeutic amount of a mitochondria targeted antioxidant; and
   c) wherein achieving the predetermined normal conduction velocity reduces arrhythmic risk in the individual.

2. The method of claim 1, wherein the amount of antioxidant is effective to reduce arrhythmic risk.

3. The method of claim 1, wherein the antioxidant prevents or lowers reduction in sodium channel current ($I_{Na}$) by reducing or suppressing mitochondrial ROS production.

4. The method of claim 1, wherein the antioxidant is administered orally or intravenously.

5. The method of claim 1, wherein the individual is suffering from arrhythmia.

6. The method of claim 1, wherein the antioxidant comprises at least one member selected from the group consisting of a powder, a tablet, a capsule, a solution, a suspension, and an injectable formulation.

7. The method of claim 1, wherein the antioxidant comprises 2-(2,2,6,6-Tetramethylpiperidin-1-oxyl-4-ylamino)-2-oxoethyl)triphenylphosphonium chloride (MitoTEMPO).

8. The method of claim 1, wherein the individual is a person.

9. A method of reducing arrhythmic risk in an individual with cardiomyopathy characterized by an enlarged chamber and reduced sodium channel current, comprising the steps of:
   a) providing an individual with said cardiomyopathy and reduced sodium channel current;
   b) restoring the sodium channel current to a predetermined normal by improving the conduction velocity by administering to the individual a therapeutic amount of a mitochondria targeted antioxidant; and
   c) wherein achieving the predetermined normal sodium channel current reduces arrhythmic risk in the individual.

10. The method of claim 9, wherein the amount of antioxidant is effective to reduce arrhythmic risk.

11. The method of claim 9, wherein the antioxidant prevents or lowers reduction in sodium channel current ($I_{Na}$) by reducing or suppressing mitochondrial ROS production.

12. The method of claim 9, wherein the antioxidant is administered orally or intravenously.

13. The method of claim 9, wherein the individual is suffering from arrhythmia.

14. The method of claim 9, wherein the antioxidant comprises at least one member selected from the group consisting of a powder, a tablet, a capsule, a solution, a suspension, and an injectable formulation.

15. The method of claim 9, wherein the antioxidant comprises 2-(2,2,6,6-Tetramethylpiperidin-1-oxyl-4-ylamino)-2-oxoethyl)triphenylphosphonium chloride (MitoTEMPO).

16. The method of claim 9, wherein the individual is a person.

17. A method of reducing arrhythmic risk in an individual with cardiomyopathy characterized by an enlarged chamber and a cardiac ejection fraction of less than 50%, comprising the steps of:
   a) providing an individual with said cardiomyopathy and a cardiac ejection fraction of less than 50%;
   b) restoring the cardiac ejection fraction to more than 50% by improving the conduction velocity by administering to the individual a therapeutic amount of a mitochondria targeted antioxidant; and
   c) wherein achieving a cardiac ejection fraction of more than 50% reduces arrhythmic risk in the individual.

18. The method of claim 17, wherein the amount of antioxidant is effective to reduce arrhythmic risk.

19. The method of claim 17, wherein the antioxidant prevents or lowers reduction in sodium channel current ($I_{Na}$) by reducing or suppressing mitochondrial ROS production.

20. The method of claim 17, wherein the antioxidant is administered orally or intravenously.

21. The method of claim 17, wherein the individual is suffering from arrhythmia.

22. The method of claim 17, wherein the antioxidant comprises at least one member selected from the group consisting of a powder, a tablet, a capsule, a solution, a suspension, and an injectable formulation.

23. The method of claim 17, wherein the antioxidant comprises 2-(2,2,6,6-Tetramethylpiperidin-1-oxyl-4-ylamino)-2-oxoethyl)triphenylphosphonium chloride (MitoTEMPO).

24. The method of claim 17, wherein the individual is a person.

\* \* \* \* \*